(12) United States Patent
Yang et al.

(10) Patent No.: US 10,206,863 B2
(45) Date of Patent: Feb. 19, 2019

(54) CATIONIC ARABINOXYLANS, THEIR HYDROPHOBICALLY MODIFIED PRODUCTS, AND PREPARATION METHOD AND APPLICATION THEREOF

(71) Applicant: Evonik Degussa GmbH, Essen (DE)

(72) Inventors: Cheng Yang, Wuxi (CN); Weiyi Cui, Qiqihar (CN)

(73) Assignee: EVONIK DEGUSSA GMBH, Essen (DE)

( * ) Notice: Subject to any disclaimer, the term of this patent is extended or adjusted under 35 U.S.C. 154(b) by 0 days.

(21) Appl. No.: 15/310,267

(22) PCT Filed: May 21, 2015

(86) PCT No.: PCT/CN2015/079478
§ 371 (c)(1),
(2) Date: Nov. 10, 2016

(87) PCT Pub. No.: WO2015/176671
PCT Pub. Date: Nov. 26, 2015

(65) Prior Publication Data
US 2017/0143609 A1    May 25, 2017

(30) Foreign Application Priority Data

May 22, 2014  (CN) .......................... 2014 1 0218644

(51) Int. Cl.
*A61K 38/00* (2006.01)
*C07K 14/435* (2006.01)
*C07K 14/47* (2006.01)
*A61K 8/73* (2006.01)
*A61Q 19/10* (2006.01)
*A61Q 5/02* (2006.01)
*A61Q 5/12* (2006.01)
*C08B 37/00* (2006.01)

(52) U.S. Cl.
CPC ................. *A61K 8/73* (2013.01); *A61Q 5/02* (2013.01); *A61Q 5/12* (2013.01); *A61Q 19/10* (2013.01); *C08B 37/0057* (2013.01); *A61K 2800/262* (2013.01); *A61K 2800/5426* (2013.01)

(58) Field of Classification Search
CPC .......... A61K 38/00; A61Q 5/02; A61Q 19/10; C08B 37/0057
See application file for complete search history.

(56) References Cited

U.S. PATENT DOCUMENTS

| | | |
|---|---|---|
| 6,388,069 B1 | 5/2002 | Buchanan et al. |
| 7,879,994 B2 | 2/2011 | Buchanan et al. |
| 8,816,066 B2 | 8/2014 | Buchanan et al. |
| 9,040,683 B2 | 5/2015 | Buchanan et al. |
| 9,040,684 B2 | 5/2015 | Buchanan et al. |
| 9,040,685 B2 | 5/2015 | Buchanan et al. |
| 9,150,665 B2 | 10/2015 | Buchanan et al. |
| 9,243,072 B2 | 1/2016 | Buchanan et al. |
| 2004/0151681 A1 | 8/2004 | Busk et al. |

FOREIGN PATENT DOCUMENTS

| | | |
|---|---|---|
| CN | 1886427 A | 12/2006 |
| CN | 104327197 A | 2/2015 |
| WO | 2010108206 A1 | 9/2010 |
| WO | 2015176671 A1 | 11/2015 |

OTHER PUBLICATIONS

Ebringerova et al. (World Journal of Microbiology & Biotechnology, 640-644, 1994).*
Ebringerova et al. (Carbohydrate Polymers, pp. 301-308, published 1994).*
International Search Report dated Sep. 2, 2015 in PCT/CN2015/079478 (3 pages).
Written Opinion dated Sep. 2, 2015 in PCT/CN2015/079478 (6 pages).
European Search Report dated Oct. 18, 2017 in EP 15796335.6 (5 pages).

* cited by examiner

*Primary Examiner* — Alma Pipic
(74) *Attorney, Agent, or Firm* — Nexsen Pruet, PLLC; Philip P. McCann

(57) ABSTRACT

The present invention provides a cationic arabinoxylan and the hydrophobically modified product thereof. The cationic arabinoxylan is prepared based on a cereal arabinoxylan and a quaternizing agent, with water as solvent and strong alkali as catalyst. The hydrophobically modified product is prepared based on cationic arabinoxylan and alkyl halide, with pyridine as catalyst. Said cationic arabinoxylan and the hydrophobically modified product thereof can be used as a conditioning agent or thickener in cosmetics or personal care compositions, and can also be used in textile, papermaking, pharmaceutical and food industry applications.

8 Claims, 6 Drawing Sheets

US 10,206,863 B2

CATIONIC ARABINOXYLANS, THEIR HYDROPHOBICALLY MODIFIED PRODUCTS, AND PREPARATION METHOD AND APPLICATION THEREOF

This application is a national stage application under 35 U.S.C. § 371 of International Application No. PCT/CN2015/079478 filed 21 May 2015, which claims priority to Chinese Application No. 201410218644.8 filed 22 May 2014, the disclosures of which are expressly incorporated herein by reference.

TECHNICAL FIELD

The present invention relates to arabinoxylan derivatives, their hydrophobic modification product and preparation and application thereof. Particularly, the invention relates to preparation of cationic arabinoxylan derivatives which have conditioning and thickening function in cosmetics and personal care formulations.

BACKGROUND

Cationic polymers have been used widely in fields like cosmetics and personal care, water treatment, papermaking and oil chemistry.

Cationic conditioners are the key component of the shampoo. Cationic polymers are the main kind of cationic conditioner which improve conditioning, combability and provide softness and smoothness for hair. Because the electrostatic interaction between positive charged cationic polymers and the negative charged hair surface, cationic polymers can adsorb on the hair surface and improve the combability and ameliorate electrostatic charging of the hair. On the other hand, when diluting the shampoo, complex coacervates will be formed between the cationic polymers and anionic surfactants. These complex coacervates can help silicone oil and other functional ingredients to deposit on the hair surface to soften, smooth and repair the hair. Molecular weight and charge density of cationic polymer are key factors which influence the adsorption of cationic polymer and deposition of silicone oil on hair surface. The previous works show that cationic polymer with smaller molecular weight and higher charge density can adsorb on hair more quickly and the adsorbed amount is higher, whereas cationic polymer with larger molecular weight and moderate charge density favors deposition of silicone oil on hair. Cationic cellulose derivatives and cationic guar gum are two kind of main commercial cationic polymeric conditioner in shampoo. However, these cationic nature polymers are expensive.

In addition, they have some drawbacks due to limitation of molecular structure of nature polymer. For example, the solution of cationic guar gum is not clear so that it cannot be used in transparent shampoo formulation. Therefore, development of cationic polymeric conditioners with low price as well as excellent function is still a challenge.

Arabinoxylans are the main hemicelluloses of cereal cell walls and can be widely found in cereal bran and endosperm. The basic structure of arabinoxylans consists of a linear $(1\rightarrow 4)$-$\beta$-D-linked xylopyranosyl (Xylp) backbone, with $\alpha$-L-arabinofuranosyl (Araf) side units attached to O-3 and/or O-2 of backbone Xylp units. In addition, a few ferulic acid groups may be attached to the Araf units. The type of substitution of arabinoxylans, whether consisting of single Araf branches or larger and more structurally complicated branches, varies depending on the source of arabinoxylans. The molecular weight of cereal arabinoxylans varies from tens of thousands to several millions (g/mol) depending on the source of arabinoxylans. Due to the advantages like wide accessible raw material, diversity structure, inexpensive, biocompatible, nontoxic, film building, antioxidation and bioactive of cereal arabinoxylans, they have important potential to be used in the cosmetics, pharmaceutical, and food industry.

U.S. Pat. No. 6,388,069 B1 disclosed a method of extracting arabinoxylan from corn fiber and the methods of preparing novel arabinoxylan esters and ethers. However, the invention does not involve the synthesis, hydrophobic modification and application of cationic cereal arabinoxylans.

SUMMARY OF THE INVENTION

The objective of this invention is to provide a type of cationic arabinoxylans their hydrophobically modified derivatives, and their application in fields such as cosmetics and personal care.

According to this invention, there provides a water soluble cationic arabinoxylan with conditioning effect, wherein the hydrogen atoms of the hydroxyl side groups of xylopyranosyl (Xylp) residues and $\alpha$-L-arabinofuranosyl (Araf) residues are both partially substituted by quaternizing groups of a quaternizing agent. Preferably, the weight average molecular weight of the cationic arabinoxylan is $\geq 100,000$ g/mol; preferably the weight average molecular weight is smaller than 2,000,000 g/mol.

Weight average molecular weight for polymers described in the instant invention is determined by Gel Permeation Chromatography (GPC) with Pullulan standards.

The cationic arabinoxylan of the present invention can be schematically represented by structure formula below:

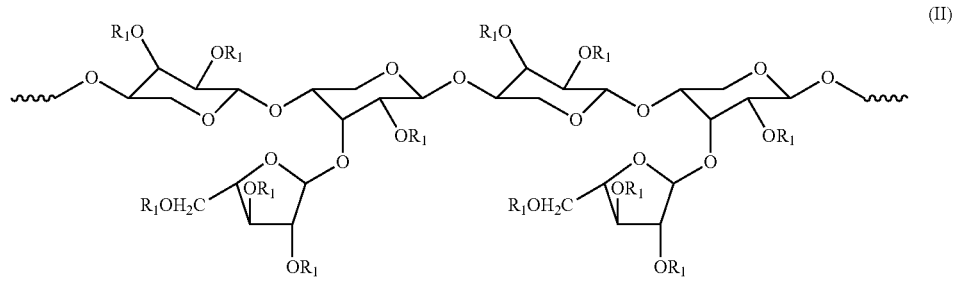

(II)

Wherein $R_1$ each independently represents H or R', provided that not all of $R_1$ is H, or is R' simultaneously; and wherein R' is a quaternizing group, for example, its structure can be represented as following:

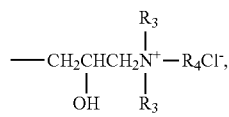

Wherein $R_3$ each independently represents methyl or ethyl, and $R_4$ is selected from methyl, ethyl, butyl, octyl, dodecyl, and cetyl, provided that when $R_3$ is ethyl, $R_4$ is ethyl only. Examples of the quaternizing group can be selected from —$CH_2CH(OH)CH_2N^+(CH_3)_3Cl^-$, —$CH_2CH(OH)CH_2N^+(CH_3)_2C_2H_5Cl^-$, —$CH_2CH(OH)CH_2N^+(C_2H_5)_3Cl^-$, —$CH_2CH(OH)CH_2N^+(CH_3)_2C_{16}H_{33}Cl^-$, etc.

The invention also provides a method for preparation of a cationic arabinoxylan. The method comprises the steps of:

(1) Dissolving an arabinoxylan and 0.5-4.0 wt %, preferably 2.0-2.8 wt %, of a strong alkali into water;

(2) Adding a quaternizing agent with the molar ratio of the quaternizing agent and anhydroxylose unit of the arabinoxylan being from 0.2:1 to 5:1, preferably 2:1 to 4:1, and reacting for 2-8 h, preferably 4-7 h, at 20-65° C., preferably 20-35° C.; and (3) Separating the cationic arabinoxylan as reaction product.

The mentioned arabinoxylan is a water soluble arabinoxylan, preferably its weight average molecular weight is ≥100,000 g/mol, preferably the weight average molecular weight is smaller than 2,000,000 g/mol, its Araf/Xylp (i.e. molar ratio of Araf residues to Xylp residues) preferably is 0.4~1.2, for example, 0.5~1.0, 0.5~0.95, 0.5~0.93, 0.6~1.0, 0.6~0.95, 0.6~0.93, 0.7~1.0, 0.7~0.95, or 0.7~0.93. The arabinoxylan is preferably a water soluble cereal arabinoxylan. The cereal arabinoxyan can be selected from, for example, water soluble arabinoxylans extracted from corn bran, wheat bran, corn endosperm, wheat endosperm, barley endosperm, rye endosperm, triticale endosperm or oat endosperm.

In some embodiments, in step (1), the concentration of arabinoxylan in water solution is 1-30 wt %, preferably 2-15 wt %, based on the total weight of arabinoxylan and water.

In this invention, strong alkali is used as catalyst and generally is alkali hydroxide, the examples include but not limited to NaOH and KOH. The catalyst can be added in the form of either solid or aqueous solution. The amount of strong alkali is based on the total weight of strong alkali, arabinoxylan and water.

The dissolving of arabinoxylan is very slow due to the strong intermolecular hydrogen bond interaction of arabinoxylan. Therefore, heating can be used to improve the dissolving of arabinoxylan, until the arabinoxylan is fully dissolved. Preferably, in step (1), heating is used to improve the dissolving of arabinoxylan. Moreover, stirring can be used to improve the dissolving of arabinoxylan. In some embodiments, in step (1), the water solution is stirred at 50-80° C. to form a homogeneous solution after the catalyst is added. In some embodiments, the stirring time is 20-40 min.

In step (1), there is no requirement to the sequence of dissolving strong alkali and arabinoxylan. The two can be added into water simultaneously, or strong alkali can be added first, or arabinoxylan can be added first.

Typically, in step (2), the reaction is performed with stirring.

In some embodiments, in step (3), the pH value of solution is adjusted to around 7 after the reaction is finished. Typically, in step (3), the mixture of step (3) is cooled down, for example to room temperature, before adjusting pH. In some embodiments, in step (3), after the reaction is finished, the acid used to adjust the pH value of solution is HCl or $H_2SO_4$, for example, 0.1 mol/L HCl aqueous solution.

In step (3), the preferred separation method is by precipitation. In some embodiments, in step (3), cationic arabinoxylan is obtained by precipitation with ethanol. Thereafter, the precipitate can be subjected to post processing such as filtration and drying (such as vacuum drying). Preferably, 95% ethanol is used, to precipitate a white floccular precipitation. After filtration, the precipitate is dried in vacuum to obtain the cationic arabinoxylan.

In this invention, the quaternizing agent can be selected from regular quaternizing agent, for example, its structure can be represented as following:

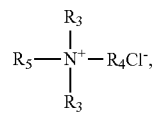

wherein $R_3$ each independently represents methyl or ethyl, and $R_4$ is selected from the group of methyl, ethyl, butyl, octyl, dodecyl, and cetyl, provided that when $R_3$ is ethyl, the $R_4$ is ethyl only, $R_5$ is

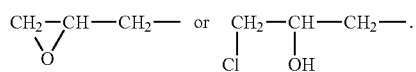

The examples of the quaternizing agent can be selected from N-(3-chloro-2-hydroxypropyl)-N,N,N-trimethylammonium chloride, N-glycidyl-N,N,N-trimethylammonium chloride, N-glycidyl-N,N-dimethyl-N-ethylammonium chloride, N-glycidyl-N,N,N-triethyl ammonium chloride, N-glycidyl-N,N-dimethyl-N-cetylammonium chloride etc.

The content of Araf and Xylp residues can be determined according to methods described in, for example: Total Dietary Fiber-Determined as Neutral Sugar Residues, Uronic Acid Residues, and Klason Lignin (Uppsala Method), AACC International Official Method 32-25 (2000), *AACC International: Approved Methods of the American Association of Cereal Chemists*, 10th ed.; AACC International Press: St. Paul, Minn.; *Journal of Cereal Science*, 1995, 21, 195-203; and *Carbohydrate Polymers*, 1994, 24, 61-71.

The degree of substitution (DS) of cationic group of the cationic arabinoxylans of the present invention is preferably: 0.03~1.0, for example, 0.03~0.8, 0.04~0.8, 0.04~0.7, 0.04~0.6, 0.06~0.6, 0.08~0.6, or 0.3~0.6. Preferably, the cationic arabinoxylans have high degree of substitution of cationic group, for example, 0.3-0.57, to get a better conditioning effect. The method to determine the degree of substitution of cationic group can refer to, for example, *Journal of Applied Polymer Science*, 1998, 67, 1523-1530, and *Carbohydrate Polymers*, 2010, 82, 965-975.

In the cationic arabinoxylans of the present invention, the hydrogen atoms of hydroxyl side groups of Araf residues and Xylp residues are both partially substituted by quaternizing groups of a quaternizing agent. For Xylp residues, O-3 and/or O-2 of Xylp residues are substituted by quaternizing group. For Araf residues, any hydroxyl groups of Araf residues can be substituted. The degree of substitution of cationic group is defined as the average number of hydroxyl group(s) substituted by quaternizing group of quaternizing agent in each Xylp residue, including the Araf residue attached thereto, if any in a cationic arabinoxylan molecule.

This invention also provides a cationic arabinoxylan prepared by method described above.

The cationic arabinoxylans of the present invention can form a transparent water solution, therefore they can be used to prepare transparent personal care or cosmetics products, such as shampoo.

The synthesis route of cationic arabinoxylans can be schematically shown as following: (1)

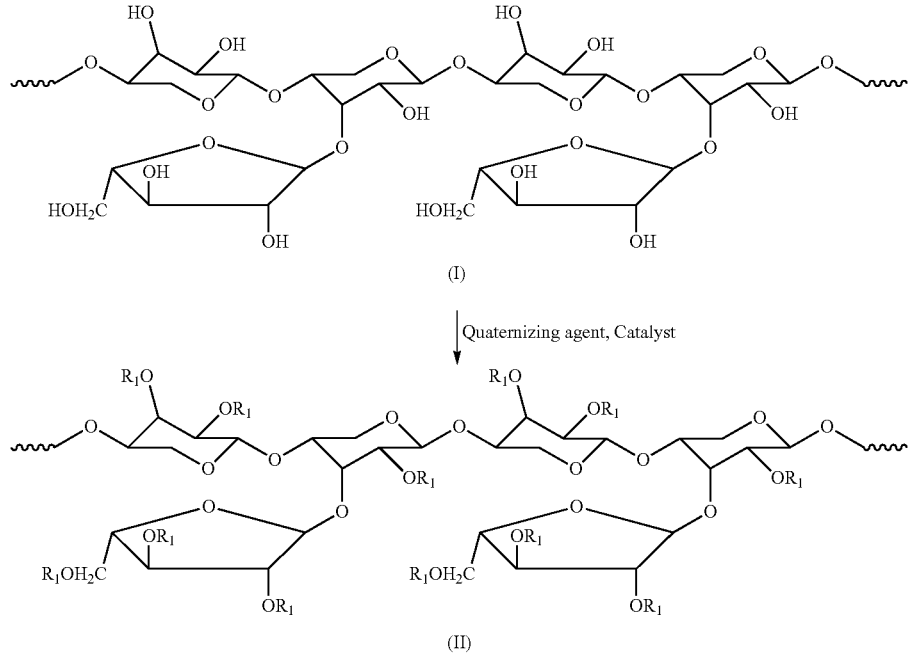

Wherein $R_1$ each independently represent H or R', provided that not all of $R_1$ is H, or is R' simultaneously; wherein R' is a quaternizing group as defined above.

According to this invention, there provides an alkylated cationic arabinoxylan, wherein the hydrogen atoms of hydroxyl side groups of Araf and Xylp residues are both partially substituted by quaternizing groups of a quaternizing agent, meanwhile, other hydrogen atoms of hydroxyl side groups are partially substituted by alkylating groups. The mentioned alkylating group can be represented as $-CH_2(CH_2)_nCH_3$, wherein n is an even number from 2 to 16, for example, n is an even number from 2 to 14. The mentioned alkylated cationic arabinoxylans are water soluble alkylated cationic arabinoxylans with conditioning and thickening function.

The chemical structure of the alkylated cationic arabinoxylans (i. e. hydrophobically modified cationic arabinoxylans) of the present invention can be schematically represented as follows:

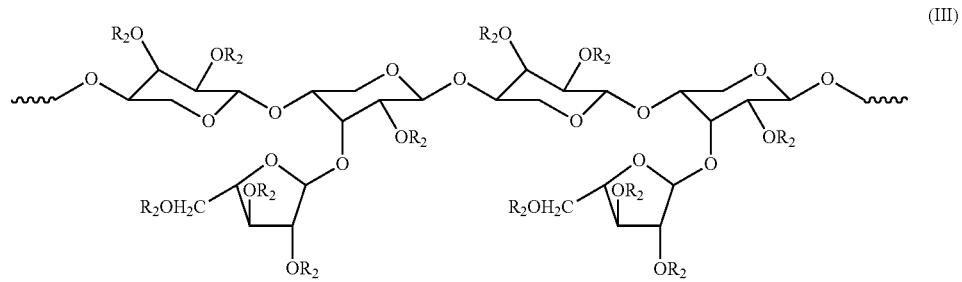

Wherein $R_2$ each independently represent H, R', or —$CH_2$($CH_2$)$_n$$CH_3$ (wherein n is an even number from 2 to 16), provided that not all of $R_1$ is or is not H simultaneously, or is or is not R' simultaneously, or is or is not —$CH_2$($CH_2$)$_n$$CH_3$ simultaneously (i.e. provided that $R_2$ of the molecule includes three kinds of substituted groups, which partially are H, partially are R' and partially are —$CH_2$($CH_2$)$_n$$CH_3$), wherein R' is the quaternizing group as defined above.

The present invention also provides a method for preparation of the hydrophobically modified cationic arabinoxylans. The method comprises the steps of:

(1) Dissolving a cationic arabinoxylan in dimethyl sulfoxide (DMSO) to form a 1-30 wt %, preferably 2-15 wt % solution of cationic arabinoxylan;

(2) Adding pyridine to the solution as catalyst, and adding an alkyl halide as an alkylating agent with the molar ratio of the alkylating agent and anhydroxylose units of the cationic arabinoxylan being from 0.2:1-6:1, preferably 3:1-5:1 or 4:1-5:1;

(1) Reacting for 1-8 h, preferably 3-5 h, at 30-60° C., preferably 40-50° C.; and (2) Separating the hydrophobically modified cationic arabinoxylan as reaction product.

Preferably, the mentioned cationic arabinoxylans are prepared according to the method of the invention, or the cationic arabinoxylans according to the present invention.

Preferably, the Araf/Xylp (i.e. molar ratio of Araf to Xylp residues) is 0.5~1.0, for example 0.5~0.95, 0.5~0.93, 0.6~1.0, 0.6~0.95, 0.6~0.93, 0.7~1.0, 0.7~0.95, 0.7~0.93, etc.

Preferably, the alkylating agent is alkyl halide, for example alkyl halide with structure formula $XCH_2$($CH_2$)$_n$$CH_3$, wherein n is an even number from 2 to 16, for example, an even number from 2 to 14, and X is halogen, preferably chlorine. For example, the mentioned alkylating agents can be selected from chlorobutane, chlorohexane, chloro-octane, chlorododecane, chlorotetradecane and chlorohexadecane.

The degree of substitution by alkylating agent is preferably 0.06-0.8, for example, 0.1-0.6, 0.1-0.8, 0.3-0.8, etc. The method to determine degree of substitution by alkylating agent can refer to, for example, *Journal of Applied Polymer Science*, 1998, 67, 1523-1530, and *Carbohydrate Polymers*, 2010, 82, 965-975.

The alkylated cationic arabinoxylans of the present invention are products of substitution of cationic arabinoxylans by alkyl groups of alkylating agent, wherein the hydrogen atoms of hydroxyl side groups of Araf and Xylp residues that have not been substituted by quaternizing groups are partially substituted by the alkyl groups. The degree of substitution by alkylating agent is defined as the average number of hydroxyl group(s) substituted by alkyl group of alkylating agent in each Xylp residue, including Araf residue attached thereto, if any in an alkylated cationic arabinoxylan molecule.

Preferably, the molar ratio of alkylating agent and anhydroxylose units of cationic arabinoxylan is ≥3:1, for example 3:1-5:1, more preferably 4:1-5:1. Too much alkylating agent cannot increase the degree of substitution by alkylating agent significantly, but will increase the cost of product.

In some embodiments, in step (4), after the reaction is finished, hydrophobically modified cationic arabinoxylan is obtained by precipitation with ethanol. Thereafter, the precipitate is further filtrated, and dried (such as dried in vacuum).

This invention also provides an alkylated cationic arabinoxylan prepared by method described above.

The alkylated cationic arabinoxylans of the present invention have excellent conditioning and thickening properties, and can form transparent water solution, so that they can be used to prepare transparent personal care or cosmetics products, such as shampoo.

The synthesis of hydrophobically modified cationic arabinoxylans can be schematically shown as following:

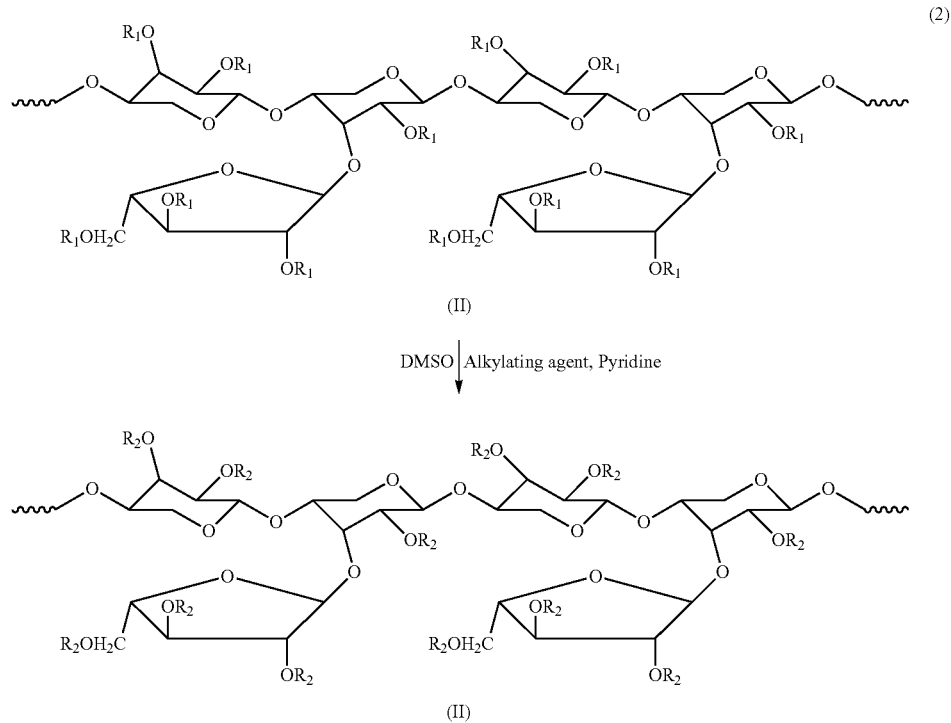

Wherein $R_2$ each independently presents H, R', or —$CH_2$(CH$_2$)$_n$CH$_3$ (wherein n is an even number from 2 to 16), provided that not all of $R_2$ is or is not H simultaneously, or is or is not R' simultaneously, or is or is not —CH$_2$(CH$_2$)$_n$CH$_3$ simultaneously (i.e. provided that $R_2$ of the molecule includes three kinds of substituted groups, which partially are H, partially are R' and partially are —CH$_2$(CH$_2$)$_n$CH$_3$), wherein R' is the quaternizing group as defined above.

This invention also provides use of the cationic arabinoxylan and/or hydrophobically modified cationic arabinoxylan of the present invention in preparation of a conditioning agent or thickener. The mentioned cationic arabinoxylan and/or hydrophobically modified cationic arabinoxylan can be used as a cationic polymer conditioning agent or thickener in cosmetics and personal care products which include shampoo, hair conditioner and bath wash etc., and can also be used in textile, papermaking, pharmaceutical and food industry applications.

This invention also provides a cosmetics or personal care composition, which comprises the cationic arabinoxylan and/or alkylated cationic arabinoxylan of the present invention, and other conventional ingredients. The conventional ingredients can be selected from surfactants, emulsifiers, oils, fats, moisturizers, hair conditioning agents, chelating agents, antidandruff agents, preservatives, colorants, fragrance, plant extracts, antioxidants, sunscreen agents, ultraviolet light absorbers, vitamins, viscosity adjusting agents, pH adjusting agents and any combinations thereof. The mentioned cationic arabinoxylan or alkylated cationic arabinoxylan can be used as a conditioning agent and/or thickener.

The present invention therefore provides a novel cationic polymer conditioning agent or thickener with cheap price and excellent properties. In this invention, the raw material arabinoxylans are widely accessible and have diverse structures. They are also inexpensive, biocompatible, nontoxic, non-irritating, with good film building, antioxidation and bioactive properties. Thus, they have great potential to be used in industries like cosmetics, pharmaceutical, and food industry.

In this invention, cationic arabinoxylans are prepared by incorporating high density of positive charge in arabinoxylans through quaternizing arabinoxylans. The cationic arabinoxylans of the present invention have better conditioning effect than polysaccharide derivatives of prior art. Due to the diversity of structure and molecular weight of arabinoxylans, the properties of cationic arabinoxylans can be adjusted in a wider range.

In this invention, alkylated cationic arabinoxylans are prepared by hydrophobically modifying cationic arabinoxylans to increase their viscosity in aqueous solution and their ability to reduce combing force. Compared with cationic arabinoxylans, alkylated cationic arabinoxylans have better conditioning and thickening properties.

In addition, the cationic arabinoxylans and alkylated cationic arabinoxylans of the present invention can form transparent solution, so that they can be used to prepare transparent formulation, such as transparent shampoo.

The cationic arabinoxylans and their hydrophobically modified derivatives of the present invention have great potential for use in cosmetics and personal care formulation as conditioning agent and thickener. They can also be used in water treatment, textile, papermaking, pharmaceutical and food industry.

DETAILED DESCRIPTION OF THE INVENTION

Figure 1:
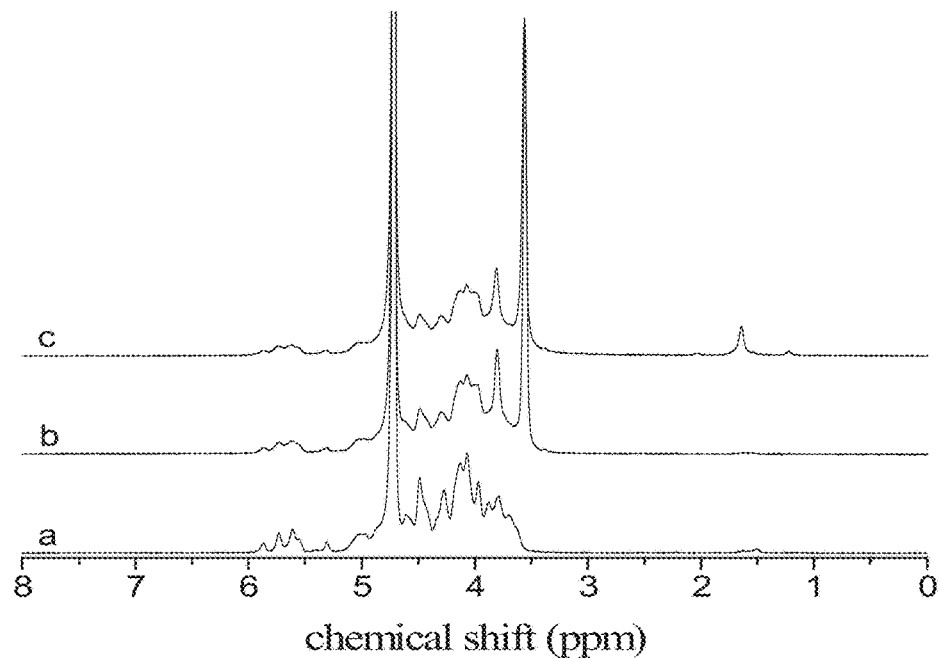
FIG. 1 shows the $^1$H-NMR spectra of corn bran arabinoxylan (a), cationic corn bran arabinoxylan (b) and hydrophobically modified cationic corn bran arabinoxylan (c).

The following examples are set forth so as to provide those of ordinary skill in the art with a complete disclosure and description of how the compounds and methods claimed herein are made and performed, and are intended to be purely exemplary of the invention and are not intended to limit the scope of what the inventors regard as their invention.

Example 1

(1) Quaternization of Cereal Arabinoxylan:

2 g (7.37 mmol anhydroxylose units) of corn bran arabinoxylan was dissolved in water to prepare a 15 wt % solution, and then solid NaOH was added into the solution as catalyst (catalyst concentration was 0.5 wt %). Stir the solution for 30 min at 50° C. and then N-(3-chloro-2-hydroxypropyl)-N,N,N-trimethylammonium chloride (11.06 mmol) (molar ratio of quaternizing agent to anhydroxylose units of arabinoxylan was 1.5:1) was added. The solution was stirred magnetically for 4 h at 45° C. Thereafter, the pH value was adjusted to 7 with 0.1 mol/L HCl solution, and then 95% ethanol was poured into the solution to obtain white floccular precipitation. After filtration, the precipitate was dried in vacuum to obtain cationic corn bran arabinoxylan (2.2 g). The elemental microanalyses results showed that C %=41.98%, H %=7.264%, N %=0.982% and the DS of cationic group was 0.16.

(2) Hydrophobic Modification of Cationic Cereal Arabinoxylan:

1 g (3.68 mmol anhydroxylose units) of the cationic corn bran arabinoxylan synthesized in (1) was dissolved in DMSO to prepare a 15 wt % solution. 1 g pyridine was added as catalyst, and lauryl chloride (9.20 mmol) (molar ratio of alkylating agent to anhydroxylose unit of cationic corn bran arabinoxylan was 2.5:1) was added into the solution. The solution was stirred for 2 h at 45° C. After the reaction was over, ethanol was poured into the solution to obtain white floccular precipitation. After filtration, the precipitate was dried in vacuum to obtain 0.85 g hydrophobically modified cationic corn bran arabinoxylan ($C_{12}$-cat-AX). The elemental microanalyses results show that C %=51.488%, H %=8.755%, N %=0.921% and the DS by alkylating agent was 0.46.

(3) Formulation of Shampoo:

A shampoo was prepared with cationic corn bran arabinoxylan prepared above. The formulation was as follows:

| Material | Content (wt %) |
| --- | --- |
| sodium alcohol ether sulphate | 20 |
| stearyl alcohol | 0.8 |
| ethylene glycol distearate | 1.5 |
| coconut monoethanol amide | 1.0 |
| cocoamidopropyl betaine | 4.0 |
| dimethicone | 1.5 |
| cationic arabinoxylan(cat-AX) | 0.5 |
| panthenol | 0.5 |
| citric acid | 0.1 |
| essence | 0.6 |
| Kathon (preservative) | 0.08 |
| deionized water | Qs to 100 |

The viscosity of the shampoo was 5000 cp (NDJ-5S viscometer, 3# rotor, 12 r/min, 25° C.). The shampoo had good stability without phase separation under 48° C. (24 h), −18° C. (24 h) heating/freeze cycle for 10 days.

A shampoo was prepared with alkylated cationic corn bran arabinoxylan as prepared above. The formulation is as follows:

| Material | Content (wt %) |
| --- | --- |
| sodium alcohol ether sulphate | 20 |
| stearyl alcohol | 0.8 |
| ethylene glycol distearate | 1.5 |
| coconut monoethanol amide | 1.0 |
| cocoamidopropyl betaine | 4.0 |
| dimethicone | 1.5 |
| alkylated cationic arabinoxylan (C12-cat-AX) | 0.5 |
| panthenol | 0.5 |
| citric acid | 0.1 |
| essence | 0.6 |
| Kathon(preservative) | 0.08 |
| deionized water | Qs to 100 |

The viscosity of the shampoo was 6500 cp (NDJ-5S viscometer, 3# rotor, 12 r/min, 25° C.). The shampoo had good stability without phase separation under 48° C. (24 h), −18° C. (24 h) heating/freeze cycle for 10 days.

Figure 9:
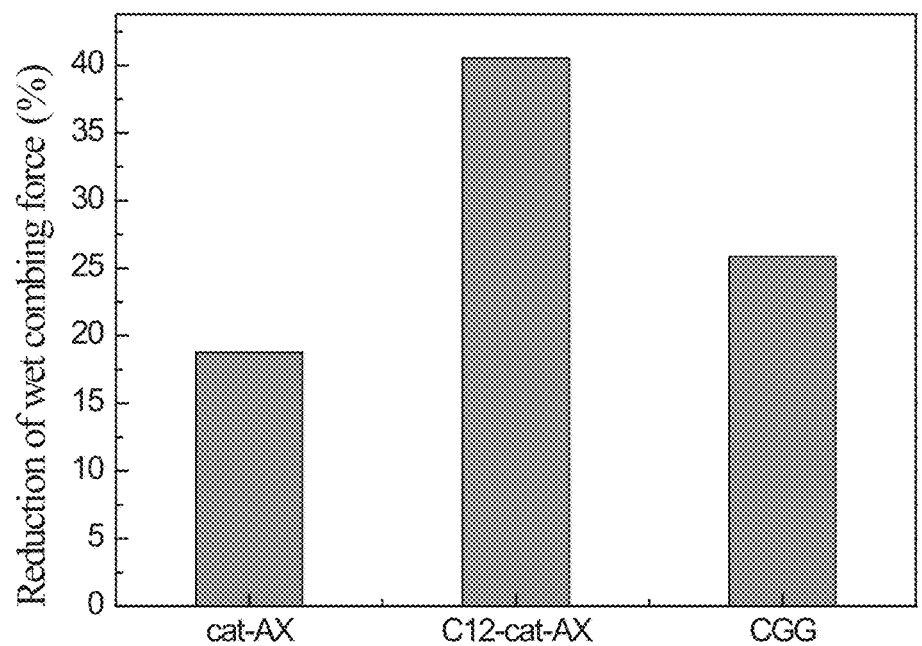
FIG. 9 shows the effect of cationic corn bran arabinoxylan and its hydrophobically modified derivatives on wet combability of shampoo.
Figure 10:
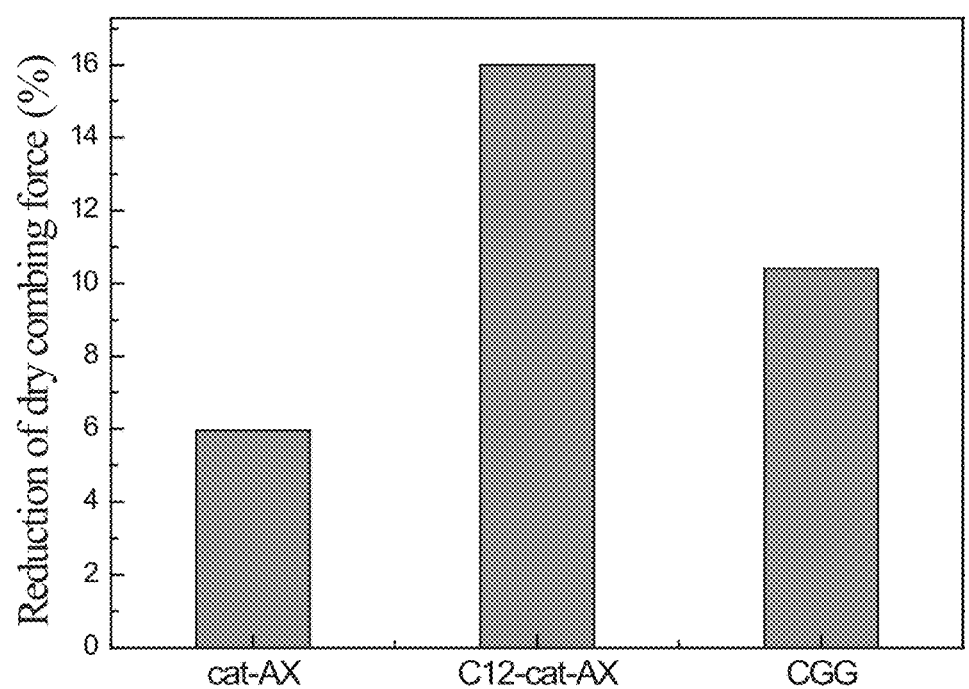
FIG. 10 shows the effect of cationic cereal arabinoxylan and its hydrophobically modified derivatives on dry combability of shampoo.

The combing testing results of the above shampoo formulation containing cationic arabinoxylan (cat-AX) and shampoo formulation containing hydrophobically modified cationic cereal arabinoxylan (C12-cat-AX) were shown in FIG. 9 and FIG. 10.

Example 2

(1) Quaternization of Cereal Arabinoxylan:

2 g (5.77 mmol anhydroxylose units) of wheat bran arabinoxylan was dissolved in water to prepare a 15 wt % solution, and then solid NaOH was added into the solution as catalyst (catalyst concentration was 4.0 wt %). Stir the solution for 30 min at 75° C. and then N-glycidyl-N,N,N-trimethylammonium chloride (1.154 mmol) (molar ratio of quaternizing agent to anhydroxylose unit of arabinoxylan was 0.2:1) was added. The solution was stirred magnetically for 4 h at 45° C. Thereafter, the pH value was adjusted to 7 with 0.1 mol/L HCl solution, and then 95% ethanol was poured into the solution to obtain white floccular precipitation. After filtration, the precipitate was dried in vacuum to obtain cationic wheat bran arabinoxylan (2.12 g). The elemental microanalyses results showed that C %=42.0%, H %=7.234%, N %=1.096% and the DS of cationic group was 0.19.

(2) Hydrophobic Modification of Cationic Cereal Arabinoxylan:

1 g (2.88 mmol anhydroxylose units) of cationic wheat bran arabinoxylan synthesized in (1) was dissolved in DMSO to prepare a 15 wt % solution and 1 g pyridine was added as catalyst, then lauryl chloride (11.52 mmol) (molar ratio of alkylating agent to anhydroxylose unit of cationic wheat bran arabinoxylan was 4:1) was added into the solution. The solution was stirred for 2 h at 45° C. After the reaction was over, ethanol was poured into the solution to obtain white floccular precipitation. After filtration, the precipitate was dried in vacuum to obtain 0.91 g hydrophobically modified cationic wheat bran arabinoxylan. The elemental microanalyses results showed that C %=53.715%, H %=9.272%, N %=0.983% and the DS by alkylating agent was 0.59.

(3) Formulation of Shampoo:

A shampoo was prepared with cationic wheat bran arabinoxylan as prepared above. The formulation was as follows:

| Material | Content (wt %) |
| --- | --- |
| sodium alcohol ether sulphate | 20 |
| stearyl alcohol | 0.8 |
| ethylene glycol distearate | 1.5 |
| coconut monoethanol amide | 1.0 |
| cocoamidopropyl betaine | 4.0 |
| dimethicone | 1.5 |
| zinc pyrithione (ZPT) | 1.0 |
| cationic arabinoxylan | 0.8 |
| citric acid | 0.1 |
| essence | 0.6 |
| Kathon(preservative) | 0.08 |
| deionized water | Qs to 100 |

The viscosity of the shampoo was 5200 cp (NDJ-5S viscometer, 3# rotor, 12 r/min, 25° C.). The shampoo had good stability without phase separation under 48° C. (24 h), −18° C. (24 h) heating/freeze cycle for 10 days. The shampoo could decrease the wet combing force by 16% and dry combing force by 5%, whereas the shampoo which used commercial cationic guar gum as conditioner and comprised the same other components as the shampoo comprising cationic arabinoxylan above decreased wet combing force by 12% and dry combing force by 3%. When determining the decrease of combing force, a shampoo without cationic polymer but comprising same other components as the shampoo comprising cationic arabinoxylan above was used as reference.

A shampoo was prepared with alkylated cationic wheat bran arabinoxylan as prepared above. The formulation is as follows:

| Material | Content (wt %) |
| --- | --- |
| sodium alcohol ether sulphate | 20 |
| stearyl alcohol | 0.8 |
| ethylene glycol distearate | 1.5 |
| coconut monoethanol amide | 1.0 |

-continued

| Material | Content (wt %) |
| --- | --- |
| cocoamidopropyl betaine | 4.0 |
| dimethicone | 1.5 |
| zinc pyrithione(ZPT) | 1.0 |
| alkylated cationic arabinoxylan | 0.8 |
| citric acid | 0.1 |
| essence | 0.6 |
| Kathon(preservative) | 0.08 |
| deionized water | Qs to 100 |

The viscosity of the shampoo was 6800 cp (NDJ-5S viscometer, 3# rotor, 12 r/min, 25° C.). The shampoo had good stability without phase separation under 48° C. (24 h), −18° C. (24 h) heating/freeze cycle for 10 days. The shampoo could decrease the wet combing force by 35% and dry combing force by 12%. When determining the decrease of combing force, a shampoo without cationic polymer but comprising same other components as the shampoo comprising cationic arabinoxylan above was used as reference.

A transparent shampoo was prepared with alkylated cationic wheat bran arabinoxylan as prepared above. The formulation is as follows:

| Material | Content (wt %) |
| --- | --- |
| sodium alcohol ether sulphate | 20 |
| cocoamidopropyl betaine | 4.0 |
| coconut monoethanol amide | 1.0 |
| dimethiconol | 0.4 |
| alkylated cationic arabinoxylan | 1.0 |
| EDTA-4Na | 0.1 |
| NaCl | 0.1 |
| citric acid | 0.1 |
| essence | 0.6 |
| dye | 0.2 |
| Kathon(preservative) | 0.08 |
| deionized water | Qs to 100 |

The viscosity of the shampoo was 5600 cp (NDJ-5S viscometer, 3# rotor, 12 r/min, 25° C.). The shampoo had good stability without phase separation under 48° C. (24 h), −18° C. (24 h) heating/freeze cycle for 10 days. The shampoo could decrease the wet combing force by 21% and dry combing force by 6%. When determining the decrease of combing force, a shampoo without alkylated cationic polymer but comprising same other components as the shampoo comprising alkylated cationic arabinoxylan above was used as reference.

Example 3

(1) Quaternization of Cereal Arabinoxylan:

2 g (7.15 mmol anhydroxylose units) of corn endosperm arabinoxylan was dissolved in water to prepare a 30 wt % solution, and then NaOH was added into the solution as catalyst (catalyst concentration was 2.5 wt %). Stir the solution for 30 min at 50° C. and then N-glycidyl-N,N,N-triethylammonium chloride (21.45 mmol)(molar ratio of quaternizing agent to anhydroxylose unit of arabinoxylan was 3:1) was added. The solution was stirred magnetically for 4 h at 45° C. Thereafter, the pH value was adjusted to 7 with 0.1 mol/L HCl solution, and then 95% ethanol was poured into the solution to obtain white floccular precipitation. After filtration, the precipitate was dried in vacuum to obtain cationic corn endosperm arabinoxylan (1.98 g). The elemental microanalyses results showed that C %=38.46%, H %=6.868%, N %=1.792% and the DS of cationic group was 0.33.

(2) Hydrophobic Modification of Cationic Cereal Arabinoxylan:

1 g (3.57 mmol anhydroxylose units) of cationic corn endosperm arabinoxylan synthesized in (1) was dissolved in DMSO to prepare a 15 wt % solution and 1 g pyridine was added as catalyst, then butyl chloride (2.49 mmol) (molar ratio of alkylating agent to anhydroxylose unit of cationic corn endosperm arabinoxylan was 0.7:1) was added into the solution. The solution was stirred for 3 h at 40° C. After the reaction was over, ethanol was poured into the solution to obtain white floccular precipitation. After filtration, the precipitate was dried in vacuum to obtain 0.92 g hydrophobically modified cationic corn endosperm arabinoxylan. The elemental microanalyses results showed that C %=43.13%, H %=7.672%, N %=1.722% and the DS by alkylating agent was 0.53.

(3) Formulation of Hair Conditioner:

A hair conditioner was prepared with cationic corn endosperm arabinoxylan prepared above. The formulation was as follows:

| Material | Content (wt %) |
| --- | --- |
| bis-aminopropyl dimethicone | 3.5 |
| stearyl alcohol | 2.5 |
| docosyltrimethylammonium chloride | 2.5 |
| cetyl alcohol | 1.5 |
| polydimethylsiloxane | 1.0 |
| cationic arabinoxylan | 2.0 |
| panthenol | 0.3 |
| EDTA-2Na | 0.1 |
| essence | 0.6 |
| Kathon(preservative) | 0.08 |
| deionized water | Qs to 100 |

The viscosity of the hair conditioner was 32630 cp (NDJ-5S viscometer, 3# rotor, 12 r/min, 25° C.). The hair conditioner had good stability without phase separation under 48° C. (24 h), −18° C. (24 h) heating/freeze cycle for 10 days. The hair conditioner could decrease the wet combing force by 20% and dry combing force by 12%. When determining the decrease of combing force, a hair conditioner without cationic polymer but comprising same other components as the hair conditioner comprising cationic arabinoxylan above was used as reference.

A hair conditioner was prepared with alkylated cationic corn endosperm arabinoxylan as prepared above. The formulation is as follows:

| Material | Content (wt %) |
| --- | --- |
| bis-aminopropyl dimethicone | 3.5 |
| stearyl alcohol | 2.5 |
| docosyltrimethylammonium chloride | 2.5 |
| cetyl alcohol | 1.5 |
| polydimethylsiloxane | 1.0 |
| alkylated cationic arabinoxylan | 2.0 |
| panthenol | 0.3 |
| EDTA-2Na | 0.1 |
| essence | 0.6 |
| Kathon (preservative) | 0.08 |
| deionized water | Qs to 100 |

The viscosity of the hair conditioner was 35630 cp (NDJ-5S viscometer, 3# rotor, 12 r/min, 25° C.). The hair conditioner had good stability without separation under 48° C. (24 h), −18° C. (24 h) heating/freeze cycle for 10 days. The hair conditioner could decrease the wet combing force by 40% and dry combing force by 20%. When determining the decrease of combing force, a hair conditioner without alkylated cationic polymer but comprising same other components as the hair conditioner comprising alkylated cationic arabinoxylan above was used as reference.

Example 4

(1) Quaternization of Cereal Arabinoxylan:

2 g (5.45 mmol anhydroxylose units) of wheat endosperm arabinoxylan was dissolved in water to prepare a 10 wt % solution, and then solid NaOH was added into the solution as catalyst (catalyst concentration was 3.0 wt %). Stir the solution for 30 min at 60° C. and then N-(3-chloro-2-hydroxypropyl)-N,N,N-trimethylammonium chloride (13.625 mmol) (molar ratio of quaternizing agent to anhydroxylose unit of arabinoxylan was 2.5:1) was added. The solution was stirred magnetically for 8 h at 30° C. Thereafter, the pH value was adjusted to 7 with 0.1 mol/L HCl solution, and then 95% ethanol was poured into the solution to obtain white floccular precipitation. After filtration, the precipitate was dried in vacuum to obtain cationic wheat endosperm arabinoxylan (2.23 g). The elemental microanalyses results showed that C %=41.36%, H %=7.213%, N %=1.722% and the DS of cationic group was 0.19.

(2) Hydrophobic Modification of Cationic Cereal Arabinoxylan:

1 g (2.72 mmol anhydroxylose units) of cationic wheat endosperm arabinoxylan synthesized in (1) was dissolved in DMSO to prepare a 30 wt % solution and 1 g pyridine was added as catalyst, then cetyl chloride (10.86 mmol) (molar ratio of alkylating agent to anhydroxylose unit of cationic wheat endosperm arabinoxylan was 4:1) was added into the solution. The solution was stirred for 8 h at 30° C. After the reaction was over, ethanol was poured into the solution to obtain white floccular precipitation. After filtration, the precipitate was dried in vacuum to obtain 0.89 g hydrophobically modified cationic wheat endosperm arabinoxylan. The elemental microanalyses results showed that C %=52.33%, H %=9.106%, N %=1.682% and the DS by alkylating agent was 0.33.

(3) Formulation of Bath Wash:

A bath wash was prepared with cationic wheat endosperm arabinoxylan prepared above. The formulation was as follows:

| Material | Content (wt %) |
| --- | --- |
| lauric acid | 12 |
| tetradecanoic acid | 6 |
| octadecanoic acid | 1 |
| potassium hydroxide | 5.29 |
| ethylene glycol distearate | 2.0 |
| glycerol | 2.0 |
| cationic arabinoxylan | 0.5 |
| plant extracts | 1.0 |
| EDTA-4Na | 0.1 |
| citric acid | 0.1 |
| essence | 0.6 |
| antiseptic | 0.1 |
| deionized water | to 100 |

The viscosity of the bath wash was 4280 cp (NDJ-5S viscometer, 3# rotor, 12 r/min, 25° C.) and the pH value was 9.12. The bath wash had good stability without phase separation under 48° C. (24 h), −18° C. (24 h) heating/freeze cycle for 10 days. The viscosity of the bath wash increased by 30% compared with the bath wash without cationic polymer but with same other components as the bath wash comprising cationic arabinoxylan above. Moreover, the bath wash comprising cationic arabinoxylan had better stability and was more moisty after use.

A bath wash was prepared with alkylated cationic wheat endosperm arabinoxylan as prepared above. The formulation is as follows:

| Material | Content (wt %) |
| --- | --- |
| lauric acid | 12 |
| tetradecanoic acid | 6 |
| octadecanoic acid | 1 |
| potassium hydroxide | 5.29 |
| ethylene glycol distearate | 2.0 |
| glycerol | 2.0 |
| alkylated cationic arabinoxylan | 0.5 |
| plant extracts | 1.0 |
| EDTA-4Na | 0.1 |
| citric acid | 0.1 |
| essence | 0.6 |
| antiseptic | 0.1 |
| deionized water | Qs to 100 |

The viscosity of the bath wash was 6120 cp (NDJ-5S viscometer, 3# rotor, 12 r/min, 25° C.) and the pH value was 9.20. The bath wash had good stability without phase separation under 48° C. (24 h), −18° C. (24 h) heating/freeze cycle for 10 days. The viscosity of the bath wash increased by 86% compared with the bath wash without cationic polymer but with same other components as the bath wash comprising alkylated cationic arabinoxylan above. Moreover, the bath wash comprising alkylated cationic arabinoxylan had better stability and was more moisty after use.

Example 5

(1) Quaternization of Cereal Arabinoxylan:

2 g (7.12 mmol anhydroxylose units) of triticale endosperm arabinoxylan was dissolved in water to prepare a 8 wt % solution, and then solid NaOH was added into the solution as catalyst (catalyst concentration was 1.2 wt %). Stir the solution for 30 min at 60° C. and then N-glycidyl-N,N,N-trimethylammonium chloride (7.12 mmol) (molar ratio of quaternizing agent to anhydroxylose unit of arabinoxylan was 1:1) was added. The solution was stirred magnetically for 2 h at 65° C. Thereafter, the pH value was adjusted to 7 with 0.1 mol/L HCl solution, and then 95% ethanol was poured into the solution to obtain white floccular precipitation. After filtration, the precipitate was dried in vacuum to obtain cationic triticale endosperm arabinoxylan (2.17 g). The elemental microanalyses results showed that C %=42.84%, H %=7.254%, N %=1.092% and the DS of cationic group was 0.078.

(2) Hydrophobic Modification of Cationic Cereal Arabinoxylan:

1 g (3.56 mmol anhydroxylose units) of cationic triticale endosperm arabinoxylan synthesized in (1) was dissolved in DMSO to prepare a 20 wt % solution and 1 g pyridine was added as catalyst, then 1-chlorohexane (0.712 mmol) (molar ratio of alkylating agent to anhydroxylose unit of cationic triticale endosperm arabinoxylan was 0.2:1) was added into the solution. The solution was stirred for 1 h at 60° C. After the reaction was over, ethanol was poured into the solution to obtain white floccular precipitation. After filtration, the precipitate was dried in vacuum to obtain 1.05 g hydrophobically modified cationic triticale endosperm arabinoxylan. The elemental microanalyses results showed that C %=43.68%, H %=7.405%, N %=1.073% and the DS by alkylating agent was 0.06.

(3) Formulation of Bath Wash:

A bath wash was prepared with cationic triticale endosperm arabinoxylan as prepared above. The formulation was as follows:

| Material | Content (wt %) |
|---|---|
| sodium alcohol ether sulphate | 12 |
| lauryl imidazoline | 4.5 |
| ethylene glycol distearate | 1.5 |
| castor oil | 2.0 |
| butter tree oil | 1.0 |
| Cationic arabinoxylan | 2.5 |
| $V_E$ acetate | 1.5 |
| NaCl | 0.3 |
| citric acid | 0.1 |
| essence | 0.6 |
| EDTA-2Na | 0.1 |
| preservative (DMDMH) | 0.1 |
| deionized water | Qs to 100 |

The viscosity of the bath wash was 5140 cp (NDJ-5S viscometer, 3# rotor, 12 r/min, 25° C.) and the pH value was 7.20. The bath wash had good stability without phase separation under 48° C. (24 h), −18° C. (24 h) heating/freeze cycle for 10 days. The viscosity of the bath wash increased by 22% compared with the bath wash without cationic polymer but with same other components as the bath wash comprising cationic arabinoxylan above. Moreover, the bath wash comprising cationic arabinoxylan had better stability and was more moisty after use.

A bath wash was prepared with alkylated cationic triticale endosperm arabinoxylan as prepared above. The formulation is as follows:

| Material | Content (wt %) |
|---|---|
| sodium alcohol ether sulphate | 12 |
| lauryl imidazoline | 4.5 |
| ethylene glycol distearate | 1.5 |
| castor oil | 2.0 |
| butter tree oil | 1.0 |
| alkylated cationic arabinoxylan | 2.5 |
| $V_E$ acetate | 1.5 |
| NaCl | 0.3 |
| citric acid | 0.1 |
| essence | 0.6 |
| EDTA-2Na | 0.1 |
| preservative (DMDMH) | 0.1 |
| deionized water | Qs to 100 |

The viscosity of the bath wash was 7520 cp (NDJ-5S viscometer, 3# rotor, 12 r/min, 25° C.) and the pH value was 6.7. The bath wash had good stability without phase separation under 48° C. (24 h), −18° C. (24 h) heating/freeze cycle for 10 days. The viscosity of the bath wash increased by 78% compared with the bath wash without cationic polymer but with same other components as the bath wash comprising alkylated cationic arabinoxylan above. Moreover, the bath wash comprising alkylated cationic arabinoxylan had better stability and was more moisty after use.

Example 6

(1) Quaternization of Cereal Arabinoxylan:

2 g (7.37 mmol anhydroxylose units) of corn bran arabinoxylan was dissolved in water to prepare a 15 wt % solution, and then solid NaOH was added into the solution as catalyst (catalyst concentration was 2.5 wt %). Stir the solution for 30 min at 50° C. and then N-glycidyl-N,N-dimethyl-N-cetylammonium chloride (14.74 mmol) (molar ratio of quaternizing agent to anhydroxylose unit of arabinoxylan was 2:1) was added. The solution was stirred magnetically for 4 h at 45° C. Thereafter, the pH value was adjusted to 7 with 0.1 mol/L HCl solution, and then 95% ethanol was poured into the solution to obtain white floccular precipitation. After filtration, the precipitate was dried in vacuum to obtain cationic corn bran arabinoxylan (2.04 g). The elemental microanalyses results showed that C %=42.84%, H %=7.327%, N %=1.882% and the DS of cationic group was 0.57.

(2) Hydrophobic Modification of Cationic Cereal Arabinoxylan:

1 g (3.68 mmol anhydroxylose units) of cationic corn bran arabinoxylan synthesized in (1) was dissolved in DMSO to prepare a 15 wt % solution and 1 g pyridine was added as catalyst, then 1-chlorooctane (11.055 mmol) (molar ratio of alkylating agent to anhydroxylose unit of cationic arabinoxylan was 3:1) was added into the solution. The solution was stirred for 3 h at 45° C. After the reaction was over, ethanol was poured into the solution to obtain white floccular precipitation. After filtration, the precipitate was dried in vacuum to obtain 1.02 g hydrophobically modified cationic corn bran arabinoxylan. The elemental microanalyses results showed that C %=52.58%, H %=9.045%, N %=1.785% and the DS by alkylating agent was 0.71.

(3) Formulation of Cleaning Cream:

A cleaning cream was prepared with cationic corn bran arabinoxylan as prepared above. The formulation was as follows:

| Material | Content (wt %) |
|---|---|
| stearic acid | 10 |
| hexadecanoic acid | 10 |
| tetradecanoic acid | 12 |
| dodecanoic acid | 5 |
| KOH | 6 |
| glycerol | 10 |
| propylene glycol | 5 |
| Tween-60 | 2 |
| cationic arabinoxylan | 0.8 |
| EDTA-4Na | 0.1 |
| essence | 0.6 |
| antiseptic | 0.1 |
| deionized water | Qs to 100 |

The viscosity of the cleaning cream was 62150 cp (NDJ-5S viscometer, 3# rotor, 12 r/min, 25° C.) and the pH value was 9.20. The cleaning cream had good stability without phase separation under 48° C. (24 h), −18° C. (24 h) heating/freeze cycle for 10 days. The viscosity of the cleaning cream increased by 30% compared with the cleaning cream without cationic polymer but with same other components as the cleaning cream comprising cationic arabinoxylan above. Moreover, the cleaning cream comprising cationic arabinoxylan had better stability and was more moisty after use.

A cleaning cream was prepared with alkylated cationic corn bran arabinoxylan as prepared above. The formulation was as follows:

| Material | Content (wt %) |
|---|---|
| stearic acid | 10 |
| hexadecanoic acid | 10 |
| tetradecanoic acid | 12 |

| Material | Content (wt %) |
|---|---|
| dodecanoic acid | 5 |
| KOH | 6 |
| glycerol | 10 |
| propylene glycol | 5 |
| Tween-60 | 2 |
| alkylated cationic arabinoxylan | 0.8 |
| EDTA-4Na | 0.1 |
| essence | 0.6 |
| antiseptic | 0.1 |
| deionized water | to 100 |

The viscosity of the cleaning cream was 73500 cp (NDJ-5S viscometer, 3# rotor, 12 r/min, 25° C.) and the pH value was 9.15. The cleaning cream had good stability without phase separation under 48° C. (24 h), -18° C. (24 h) heating/freeze cycle for 10 days. The viscosity of the cleaning cream increased by 54% compared with the cleaning cream without cationic polymer but with same other components as the cleaning cream comprising alkylated cationic arabinoxylan above. Moreover, the bath wash comprising alkylated cationic arabinoxylan had better stability and was more moisty after use.

Example 7

(1) Quaternization of Cereal Arabinoxylan:

2 g (7.37 mmol anhydroxylose units) of corn bran arabinoxylan was dissolved in water to prepare a 15 wt % solution, and then solid NaOH was added into the solution as catalyst (catalyst concentration was 1.5 wt %). Stir the solution for 30 min at 50° C. and then N-glycidyl-N,N-dimethyl-N-ethylammonium chloride (i.e., N,N-dimethyl-N-ethyloxypropylammonium chloride) (3.685 mmol) (molar ratio of quaternizing agent to anhydroxylose unit of arabinoxylan was 0.5:1) was added. The solution was stirred magnetically for 4 h at 45° C. Thereafter, the pH value was adjusted to 7 with 0.1 mol/L HCl solution, and then 95% ethanol was poured into the solution to obtain white floccular precipitation. After filtration, the precipitate was dried in vacuum to obtain cationic corn bran arabinoxylan (2.2 g). The elemental microanalyses results showed that C %=41.98%, H %=7.264%, N %=0.982% and the DS of cationic group was 0.17.

(2) Hydrophobic Modification of Cationic Cereal Arabinoxylan:

1 g (3.68 mmol anhydroxylose units) of cationic corn bran arabinoxylan synthesized in (1) was dissolved in DMSO to prepare a 15 wt % solution and 1 g pyridine was added as catalyst, then 1-chlorotetradecane (3.68 mmol) (molar ratio of alkylating agent to anhydroxylose unit of cationic arabinoxylan was 1:1) was added into the solution. The solution was stirred for 2 h at 45° C. After the reaction was over, ethanol was poured into the solution to obtain white floccular precipitation. After filtration, the precipitate was dried in vacuum to obtain 0.93 g hydrophobically modified cationic corn bran arabinoxylan. The elemental microanalyses results showed that C %=49.33%, H %=8.545%, N %=0.973% and the DS by alkylating agent was 0.29.

(3) Formulation of Cleaning Cream:

A cleaning cream was prepared with cationic corn bran arabinoxylan as prepared above. The formulation was as follows:

| Material | Content (wt %) |
|---|---|
| Sorbitol | 15 |
| glycerol | 7 |
| potassium monoalkyl ether phosphate (35 wt %) | 12 |
| cocamidopropyl betaine | 8 |
| PEG-400 | 2 |
| cationic arabinoxylan | 5.0 |
| EDTA-2Na | 0.1 |
| essence | 0.6 |
| antiseptic | 0.00 |
| deionized water | to 100 |

The viscosity of the cleaning cream was 23500 cp (NDJ-5S viscometer, 3# rotor, 12 r/min, 25° C.) and the pH value was 6.80. The cleaning cream had good stability without phase separation under 48° C. (24 h), -18° C. (24 h) heating/freeze cycle for 10 days. The viscosity of the cleaning cream increased by 27% compared with the cleaning cream without cationic polymer but with same other components as the cleaning cream comprising cationic arabinoxylan above. Moreover, the cleaning cream comprising cationic arabinoxylan had better stability and was more moisty after use.

A cleaning cream was prepared with alkylated cationic corn bran arabinoxylan as prepared above. The formulation was as follows:

| Material | Content (wt %) |
|---|---|
| Sorbitol | 15 |
| glycerol | 7 |
| potassium monoalkyl ether phosphate (35%) | 12 |
| cocamidopropyl betaine | 8 |
| PEG-400 | 2 |
| alkylated cationic arabinoxylan | 5.0 |
| EDTA-2Na | 0.1 |
| essence | 0.6 |
| antiseptic | 0.00 |
| deionized water | to 100 |

The viscosity of the cleaning cream was 55823 cp (NDJ-5S viscometer, 3# rotor, 12 r/min, 25° C.) and the pH value was 7.20. The cleaning cream had good stability without phase separation under 48° C. (24 h), -18° C. (24 h) heating/freeze cycle for 10 days. The viscosity of the cleaning cream increased by 200% compared with the cleaning cream without cationic polymer but with same other components as the cleaning cream comprising alkylated cationic arabinoxylan above. Moreover, the bath wash comprising alkylated cationic arabinoxylan had better stability and was more moisty after use.

Example 8

(1) Quaternization of Cereal Arabinoxylan:

2 g (8.39 mmol anhydroxylose units) of barley endosperm arabinoxylan was dissolved in water to prepare a 30 wt % solution, and then solid NaOH was added into the solution as catalyst (catalyst concentration was 2.5 wt %). Stir the solution for 30 min at 50° C. and then N-glycidyl-N,N,N-triethylammonium chloride (25.19 mmol) (molar ratio of quaternizing agent to anhydroxylose unit of arabinoxylan was 3:1) was added. The solution was stirred magnetically for 4 h at 45° C. Thereafter, the pH value was adjusted to 7 with 0.1 mol/L HCl solution, and then 95% ethanol was poured into the solution to obtain white floccular precipitation. After filtration, the precipitate was dried in vacuum to obtain cationic barley endosperm arabinoxylan (1.87 g). The elemental microanalyses results showed that C %=37.47%, H %=6.635%, N %=2.392% and the DS of cationic group was 0.35.

(2) Hydrophobic Modification of Cationic Cereal Arabinoxylan:

1 g (4.19 mmol anhydroxylose units) of cationic baeley endosperm arabinoxylan synthesized in (1) was dissolved in DMSO to prepare a 15 wt % solution and 1 g pyridine was added as catalyst, then butyl chloride (2.93 mmol) (molar ratio of alkylating agent to anhydroxylose unit of cationic arabinoxylan was 0.7:1) was added into the solution. The solution was stirred for 3 h at 40° C. After the reaction was over, ethanol was poured into the solution to obtain white floccular precipitation. After filtration, the precipitate was dried in vacuum to obtain 0.97 g hydrophobically modified cationic barley endosperm arabinoxylan. The elemental microanalyses results showed that C %=43.13%, H %=7.672%, N %=2.122% and the DS by alkylating agent was 0.60.

(3) Formulation of Shampoo:

A shampoo was prepared with cationic barley endosperm arabinoxylan as prepared above. The formulation was as follows:

| Material | Content (wt %) |
|---|---|
| sodium alcohol ether sulphate | 20 |
| stearyl alcohol | 0.8 |
| ethylene glycol distearate | 1.5 |
| coconut monoethanol amide | 1.0 |
| cocoamidopropyl betaine | 4.0 |
| dimethicone | 1.5 |
| cationic arabinoxylan | 0.5 |
| panthenol | 0.5 |
| citric acid | 0.1 |
| essence | 0.6 |
| Kathon (preservative) | 0.08 |
| deionized water | to 100 |

The viscosity of the shampoo was 4300 cp (NDJ-5S viscometer, 3# rotor, 12 r/min, 25° C.). The shampoo had good stability without phase separation under 48° C. (24 h), −18° C. (24 h) heating/freeze cycle for 10 days. The shampoo could decrease the wet combing force by 28% and dry combing force by 13%. When determining the decrease of combing force, a shampoo without cationic polymer but comprising same other components as the shampoo comprising cationic arabinoxylan above was used as reference.

A shampoo was prepared with alkylated cationic barley endosperm arabinoxylan as prepared above. The formulation was as follows:

| Material | Content (wt %) |
|---|---|
| sodium alcohol ether sulphate | 20 |
| stearyl alcohol | 0.8 |
| ethylene glycol distearate | 1.5 |
| coconut monoethanol amide | 1.0 |
| cocoamidopropyl betaine | 4.0 |
| dimethicone | 1.5 |
| alkylated cationic arabinoxylan | 0.5 |
| panthenol | 0.5 |
| citric acid | 0.1 |
| essence | 0.6 |
| Kathon (preservative) | 0.08 |
| deionized water | to 100 |

The viscosity of the shampoo was 6230 cp (NDJ-5S viscometer, 3# rotor, 12 r/min, 25° C.). The shampoo had good stability without phase separation under 48° C. (24 h), −18° C. (24 h) heating/freeze cycle for 10 days. The shampoo could decrease the wet combing force by 45% and dry combing force by 18%. When determining the decrease of combing force, a shampoo without alkylated cationic polymer but comprising same other components as the shampoo comprising alkylated cationic arabinoxylan above was used as reference.

Example 9

(1) Quaternization of Cereal Arabinoxylan:

2 g (7.56 mmol anhydroxylose units) of rye arabinoxylan was dissolved in water to prepare a 8 wt % solution, and then solid NaOH was added into the solution as catalyst (catalyst concentration was 1.2 wt %). Stir the solution for 30 min at 60° C. and then N-glycidyl-N,N,N-trimethylammonium chloride (7.56 mmol) (molar ratio of quaternizing agent to anhydroxylose unit of arabinoxylan was 1:1) was added. The solution was stirred for 2 h at 65° C. Thereafter, the pH value was adjusted to 7 with 0.1 mol/L HCl solution, and then 95% ethanol was poured into the solution to obtain white floccular precipitation. After filtration, the precipitate was dried in vacuum to obtain cationic rye endosperm arabinoxylan (2.23 g). The elemental microanalyses results showed that C %=42.95%, H %=7.35%, N %=1.392% and the DS of cationic group was 0.17.

(2) Hydrophobic Modification of Cationic Cereal Arabinoxylan:

1 g (3.78 mmol anhydroxylose units) of cationic rye endosperm arabinoxylan synthesized in (1) was dissolved in DMSO to prepare a 20 wt % solution and 1 g pyridine was added as catalyst, then chlorocyclohexane (0.756 mmol) (molar ratio of alkylating agent to anhydroxylose unit was 0.2:1) was added into the solution. The solution was stirred for 1 h at 60° C. After the reaction was over, ethanol was poured into the solution to obtain white floccular precipitation. After filtration, the precipitate was dried in vacuum to obtain 1.12 g hydrophobically modified cationic rye endosperm arabinoxylan. The elemental microanalyses results showed that C %=45.98%, H %=7.623%, N %=1.299% and the DS by alkylating agent was 0.25.

(3) Formulation of Transparent Shampoo:

A transparent shampoo was prepared with cationic rye endosperm arabinoxylan as prepared above. The formulation was as follows:

| Material | Content (wt %) |
|---|---|
| sodium alcohol ether sulphate | 20 |
| cocoamidopropyl betaine | 4.0 |
| coconut monoethanol amide | 1.0 |
| dimethiconol | 0.4 |
| cationic arabinoxylan | 1.5 |
| EDTA-4Na | 0.1 |
| NaCl | 0.1 |
| citric acid | 0.1 |
| essence | 0.6 |
| dye | 0.2 |
| Kathon (preservative) | 0.08 |
| deionized water | to 100 |

The viscosity of the transparent shampoo was 3200 cp (NDJ-5S viscometer, 3# rotor, 12 r/min, 25° C.). The shampoo was transparent and had good stability without phase separation under 48° C. (24 h), −18° C. (24 h) heating/freeze cycle for 10 days. The shampoo could decrease the wet combing force by 25% and dry combing force by 6%. When determining the decrease of combing force, a shampoo without cationic polymer but comprising same other components as the shampoo comprising cationic arabinoxylan above was used as reference.

A transparent shampoo was prepared with alkylated cationic rye endosperm arabinoxylan as prepared above. The formulation was as follows:

| Material | Content (wt %) |
| --- | --- |
| sodium alcohol ether sulphate | 20 |
| cocoamidopropyl betaine | 4.0 |
| coconut monoethanol amide | 1.0 |
| dimethiconol | 0.4 |
| alkylated cationic arabinoxylan | 1.5 |
| EDTA-4Na | 0.1 |
| NaCl | 0.1 |
| citric acid | 0.1 |
| essence | 0.6 |
| dye | 0.2 |
| Kathon (preservative) | 0.08 |
| deionized water | Qs to 100 |

The viscosity of the shampoo was 5500 cp (NDJ-5S viscometer, 3# rotor, 12 r/min, 25° C.). The shampoo was transparent and had good stability without phase separation under 48° C. (24 h), −18° C. (24 h) heating/freeze cycle for 10 days. The shampoo could decrease the wet combing force by 32% and dry combing force by 8%. When determining the decrease of combing force, a shampoo without alkylated cationic polymer but comprising same other components as the shampoo comprising alkylated cationic arabinoxylan above was used as reference.

Example 10

(1) Quaternization of Cereal Arabinoxylan:

2 g (7.13 mmol anhydroxylose units) of oat endosperm arabinoxylan was dissolved in water to prepare a 15 wt % solution, and then NaOH was added into the solution as catalyst (catalyst concentration was 2.5 wt %). Stir the solution for 30 min at 50° C. and then N-glycidyl-N,N-dimethyl-N-cetylammonium chloride (14.26 mmol) (molar ratio of quaternizing agent to anhydroxylose unit of arabinoxylan was 2:1) was added. The solution was stirred for 4 h at 45° C. Thereafter, the pH value was adjusted to 7 with 0.1 mol/L HCl solution, and then 95% ethanol was poured into the solution to obtain white floccular precipitation. After filtration, the precipitate was dried in vacuum to obtain cationic oat endosperm arabinoxylan (1.96 g). The elemental microanalyses results showed that C %=48.84%, H %=8.242%, N %=1.932% and the DS of cationic group was 0.31.

(2) Hydrophobic Modification of Cationic Cereal Arabinoxylan:

1 g (3.56 mmol anhydroxylose units) of cationic oat endosperm arabinoxylan synthesized in (1) was dissolved in DMSO to prepare a 15 wt % solution and 1 g pyridine was added as catalyst, then chlorocyclooctane (10.69 mmol) (molar ratio of alkylating agent to anhydroxylose unit was 3:1) was added into the solution. The solution was stirred for 3 h at 45° C. After the reaction was over, ethanol was poured into the solution to obtain white floccular precipitation. After filtration, the precipitate was dried in vacuum to obtain 1.02 g hydrophobically modified cationic oat endosperm arabinoxylan. The elemental microanalyses results showed that C %=57.79%, H %=9.915%, N %=1.885% and the DS by alkylating agent was 0.80.

(3) Formulation of Bath Wash:

A bath wash was prepared with cationic oat endosperm arabinoxylan as prepared above. The formulation was as follows:

| Material | Content (wt %) |
| --- | --- |
| sodium alcohol ether sulphate | 12 |
| lauryl imidazoline | 4.5 |
| ethylene glycol distearate | 1.5 |
| castor oil | 2.0 |
| butter tree oil | 1.0 |
| cationic arabinoxylan | 2.5 |
| $V_E$ acetate | 1.5 |
| NaCl | 0.3 |
| citric acid | 0.1 |
| essence | 0.6 |
| EDTA-2Na | 0.1 |
| preservative (DMDMH) | 0.1 |
| deionized water | Qs to 100 |

The viscosity of the bath wash was 4380 cp (NDJ-5S viscometer, 3# rotor, 12 r/min, 25° C.) and the pH value was 7.20. The bath wash had good stability without phase separation under 48° C. (24 h), −18° C. (24 h) heating/freeze cycle for 10 days. The viscosity of the bath wash increased by 18% compared with the bath wash without cationic polymer but with same other components as the bath wash comprising cationic arabinoxylan above. Moreover, the bath wash comprising cationic arabinoxylan had better stability and was more moisty after use.

A bath wash was prepared with alkylated cationic oat endosperm arabinoxylan as prepared above. The formulation was as follows:

| Material | Content (wt %) |
| --- | --- |
| sodium alcohol ether sulphate | 12 |
| lauryl imidazoline | 4.5 |
| ethylene glycol distearate | 1.5 |
| castor oil | 2.0 |
| butter tree oil | 1.0 |
| alkylated cationic arabinoxylan | 2.5 |
| $V_E$ acetate | 1.5 |
| NaCl | 0.3 |
| citric acid | 0.1 |
| essence | 0.6 |
| EDTA-2Na | 0.1 |
| preservative (DMDMH) | 0.1 |
| deionized water | Qs to 100 |

The viscosity of the bath wash was 4848 cp (NDJ-5S viscometer, 3# rotor, 12 r/min, 25° C.) and the pH value was 7.20. The bath wash had good stability without separation under 48° C. (24 h), −18° C. (24 h) heating/freeze cycle for 10 days. The viscosity of the bath wash increased by 30% compared with the bath wash without cationic polymer but with same other components as the bath wash comprising alkylated cationic arabinoxylan above. Moreover, the bath wash comprising alkylated cationic arabinoxylan had better stability and was more moisty after use.

The Characterization of Structure

The $^1$H-NMR and $^{13}$C-NMR spectra of arabinoxylans and their derivatives were measured by AVANCE 400 nuclear magnetic resonance spectrometer (BRUKER Co., Germany), the solvent is $D_2O$.

FIG. 1 shows the $^1$H-NMR spectra of corn bran arabinoxylan (a), cationic corn bran arabinoxylan (b) and hydrophobically modified cationic corn bran arabinoxylan (c) of Example 1.

As shown in FIG. 1, compared to $^1$H-NMR spectrum of corn bran arabinoxylan (a), the $^1$H-NMR spectrum of cationic corn bran arabinoxylan (b) appears a new peak at δ=3.58 ppm, which is attributed to the proton peak of —CH$_3$ linked to N of quaternary ammonium groups. This indicates that quaternary ammonium groups have been grafted on the corn bran arabinoxylan. Compared to $^1$H-NMR spectrum of cationic corn bran arabinoxylan (b), the $^1$H-NMR spectrum of hydrophobically modified cationic corn bran arabinoxylan appears a new peak at δ=1.61 ppm, which is attributed to the proton peak of —CH$_2$— of alkyl groups. This indicates that alkyl chains have been grafted on the cationic corn bran arabinoxylan.

Figure 2:
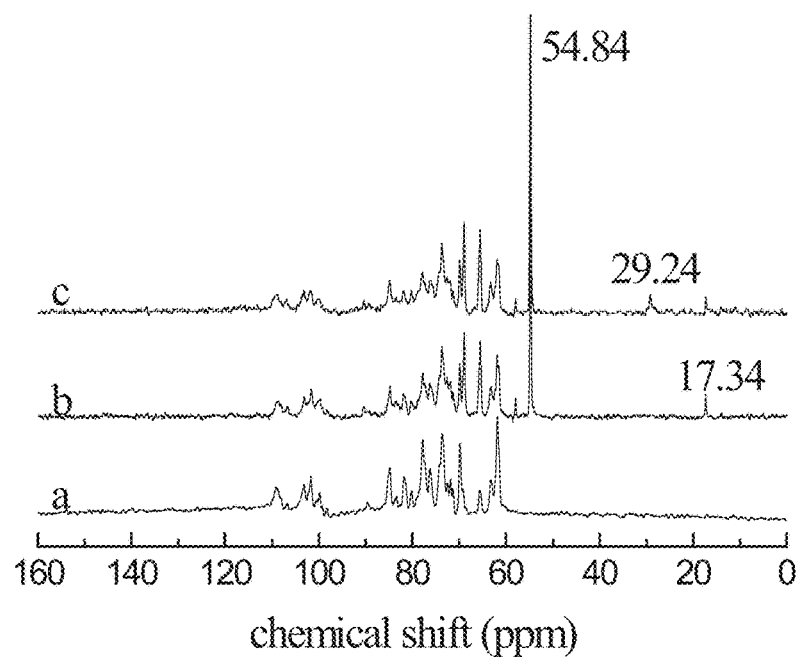
FIG. 2 shows the $^{13}$C-NMR spectra of corn bran arabinoxylan (a), cationic corn bran arabinoxylan (b) and hydrophobically modified cationic corn bran arabinoxylan (c).

FIG. 2 shows the $^{13}$C-NMR spectra of corn bran arabinoxylan (a), cationic corn bran arabinoxylan (b) and hydrophobically modified cationic corn bran arabinoxylan (c). As shown in FIG. 2, compared to $^{13}$C-NMR spectrum of corn bran arabinoxylan (a), the $^{13}$C-NMR spectrum of cationic corn bran arabinoxylan (b) appears new peaks at δ=54.87 ppm and δ=17.34 ppm, which is attributed to the carbon peak of —CH$_3$ linked to N of quaternary ammonium groups. This indicates that quaternary ammonium groups have been grafted on the corn bran arabinoxylan. Compared to $^{13}$C-NMR spectrum of cationic corn bran arabinoxylan (b), the $^{13}$C-NMR spectrum of hydrophobically modified cationic corn bran arabinoxylan appears a new peak at δ=29.24 ppm, which is attributed to the carbon peak of —CH$_2$— of alkyl groups. This indicates that alkyl chains have been grafted on the cationic corn bran arabinoxylan.

C, H, and N elemental microanalyses of cationic arabinoxylan and hydrophobically modified cationic arabinoxylan were carried out on a Vario ELIII elemental analyzer (Elementar Co., Germany). The N content (N %) and cationic DS of cationic arabinoxylans and alkylating DS of hydrophobically modified cationic arabinoxylan can be obtained by elemental microanalyses.

The Effect of Reaction Condition on the DS of Cationic Group of Cationic Arabinoxylans.

Figure 3:
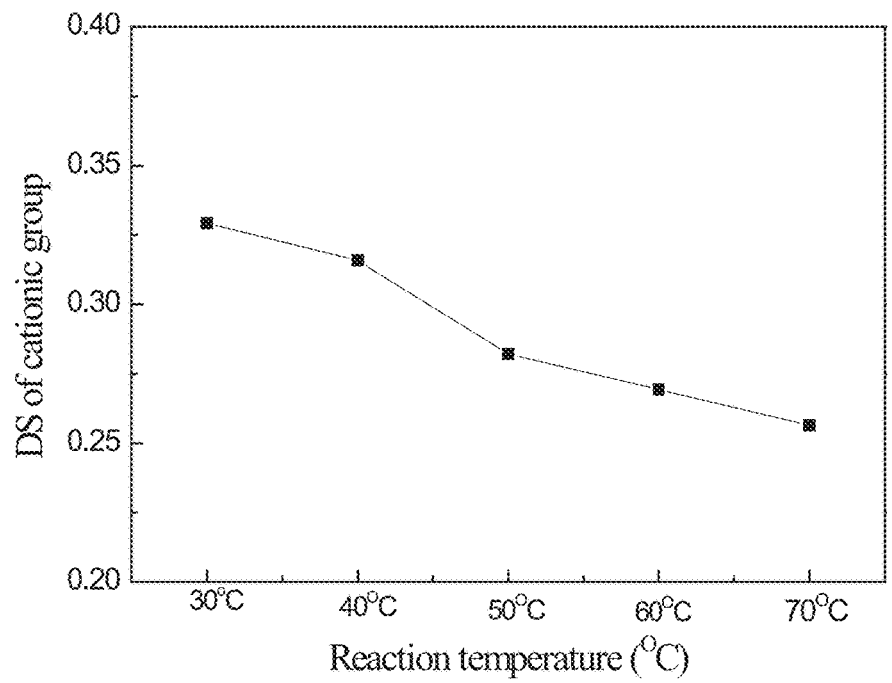
FIG. 3 shows the effect of reaction temperature on the degree of substitution of cationic group of the cationic cereal arabinoxylan.

FIG. 3 shows the effect of reaction temperature on the DS of cationic group of cationic corn bran arabinoxylan of Example 1. Along with the rise of the temperature, the DS shows a decrease. This may due to the increased side reaction at higher temperature.

Figure 4:
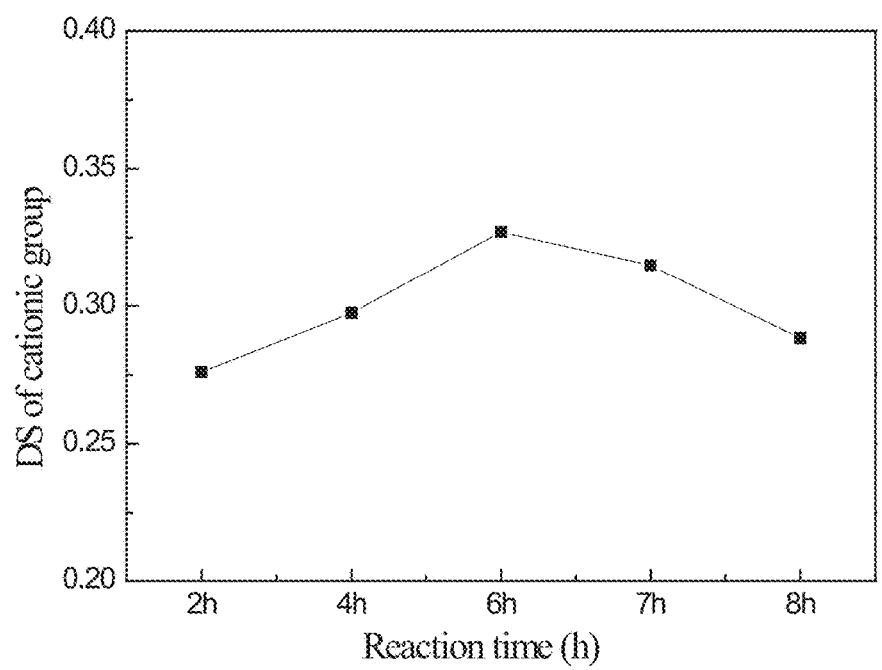
FIG. 4 shows the effect of reaction time on the DS of cationic group of the cationic cereal arabinoxylan.

FIG. 4 shows the effect of reaction time on the DS of cationic group of cationic corn bran arabinoxylan of Example 1. In the beginning, the DS rises along with the increasing of the reaction time of the reaction. However, the DS decreases when the reaction time is over 6 h. The reason may be that side reaction increases due to prolonged reaction time.

Figure 5:
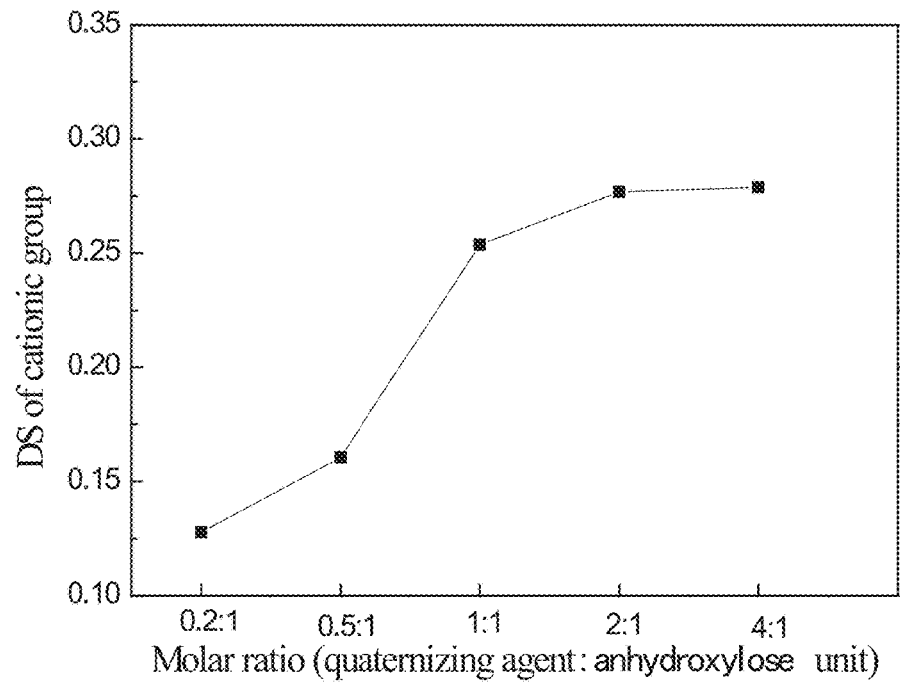
FIG. 5 shows the effect of quaternizing agent amount on the DS of cationic group of cationic cereal arabinoxylan.

FIG. 5 shows the effect of the amount of quaternizing agent on the DS by alkylating agent to cationic corn bran arabinoxylan of Example 1. The DS rises with the increasing of molar ratio of quaternizing agent and Xylp residue of arabinoxylan. However, the DS hardly rises when the amount of quaternizing agent is very high.

Figure 6:
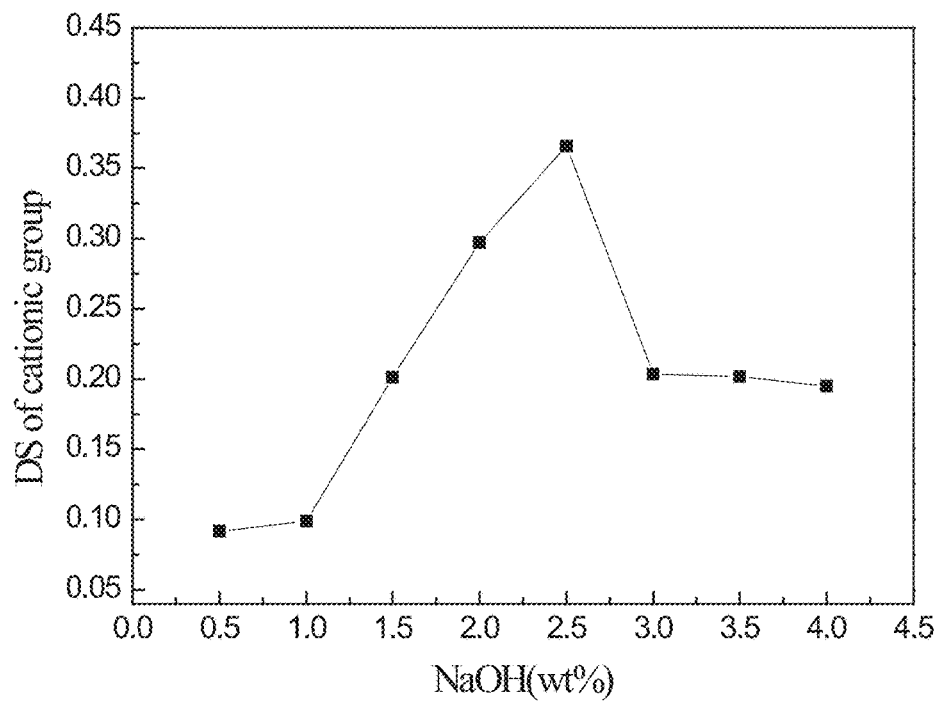
FIG. 6 shows the effect of NaOH concentration on the DS of cationic group of cationic cereal arabinoxylan.

FIG. 6 shows the effect of the concentration of catalyst NaOH on the DS of cationic group of cationic corn bran arabinoxylan. Compared with the reaction time, reaction temperature and quaternizing agent amount, the influence of NaOH concentration on DS is the most significant. FIG. 6 shows that when NaOH concentration is low, the DS of cationic group of cationic corn bran arabinoxylans increased with the increasing of NaOH concentration. As NaOH concentration is 2.5 wt %, the DS approaches to the highest value of 0.36.

Figure 7:
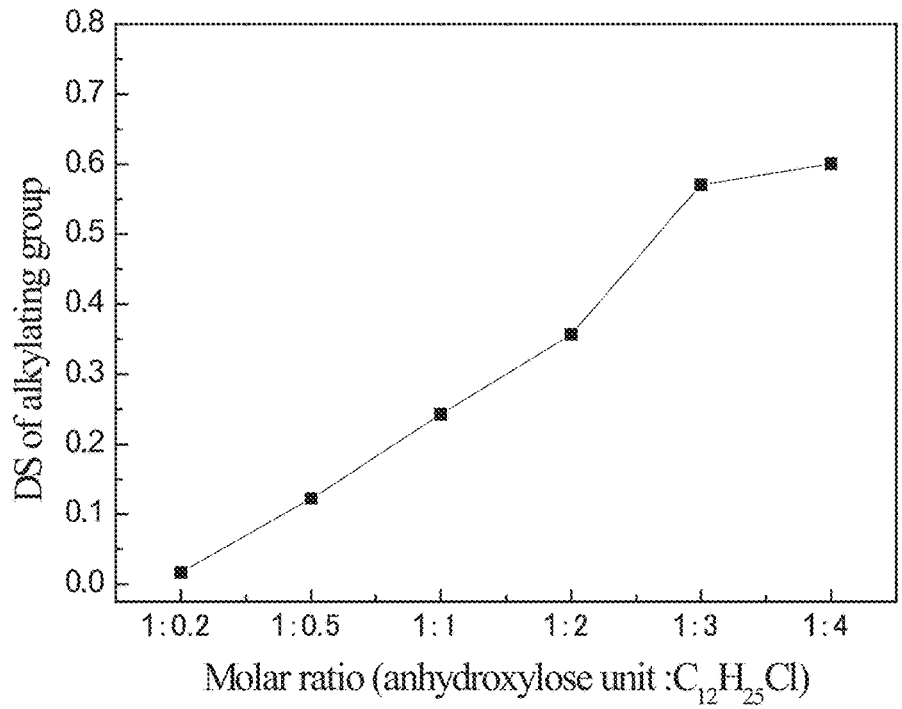
FIG. 7 shows the effect of alkylating agent concentration on the DS of alkylating group of hydrophobically modified cationic cereal arabinoxylan.

The Effect of Alkylating Agent Amount on the DS by Alkylating Agent of Hydrophobically Modified Cationic Corn Bran Arabinoxylan FIG. 7 shows the effect of alkylating agent amount on the DS by alkylating agent of hydrophobically modified cationic corn bran arabinoxylan of Example 1. In FIG. 7, cat-AX represents cationic cereal arabinoxylan.

As can be seen from FIG. 7, the amount of alkylating agent has significant influence on the DS of hydrophobically modified cationic corn bran arabinoxylan. The DS increased with the increase of alkylating agent amount. When the molar ratio of anhydroxylose unit of cationic corn bran arabinoxylan and alkylating agent is 1:4, the DS approaches to 0.60.

The Viscosity of Aqueous Solution of Cationic Arabinoxylans and their Hydrophobically Modified Derivatives The viscosity of cationic arabinoxylans and their hydrophobically modified derivatives in aqueous solution was measured with a DV-III coaxial viscometer (Brookfield). The solution concentration was 3 wt %. The viscosity measurements were performed at 25±0.1° C. with the shear rates ranging from 25 to 400 s$^{-1}$.

Figure 8:
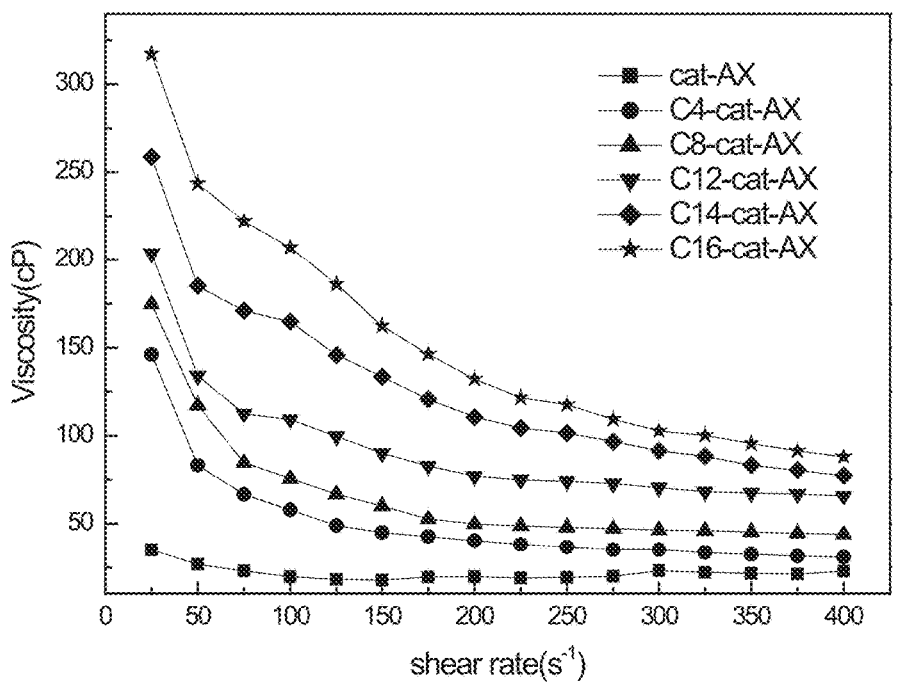
FIG. 8 shows the relationship of shear rate and viscosity of hydrophobically modified cationic cereal arabinoxylans solution with different length of alkyl chain.

Effect of Different Alkyl Chain Length on the Viscosity of Hydrophobically Modified Cationic Arabinoxylan Solution FIG. 8 shows the effect of different alkyl chain length on the viscosity of hydrophobically modified cationic corn bran arabinoxylans solution. In the figure, cat-AX stands for the cationic corn bran arabinoxylans and the $C_n$-cat-AX stands for the hydrophobically modified cationic corn bran arabinoxylans with different alkyl chain length, wherein n=4, 8, 12, 14, 16.

As shown in FIG. 8, the viscosity of the aqueous solution of hydrophobically modified cationic corn bran arabinoxylans increases when the length of alkyl chain increases, and decreases rapidly when the share rate is increased, representing the typical shear-thinning fluid behavior. The reason may be that as the length of alkyl chain increases, the $C_n$-cat-AX become more hydrophobic, which facilitates the formation of aggregates, and thus the viscosity increases. Compared with cationic arabinoxylans, hydrophobically modified cationic arabinoxylans had substantially higher viscosity, and better thickening effect.

Combing Testing

Combing testing experimentation: human hair was used to test combability. The hair tresses were about 60 g in weight and 50 cm in length. Simulating a real hair washing procedure, hair tresses were pre-wetted, and rinsed with warm water, keeping the water temperature at 40° C. 2 mL 0.5 wt % K12 (sodium dodecyl sulfate) aqueous solution was obtained with a syringe and evenly applied onto both sides of the hair tresses. Flip and knead gently both sides of the tresses for about 30 seconds, along the hair tresses (from root to tip end of hair) to remove dirt. Then the hair tresses were rinsed with warm water to remove K12 (for 1 minute, or longer if necessary) to obtain pre-washed tresses. Wash pre-washed tresses according to the procedure above with different shampoo formulations (2 mL) to be tested instead of K12, respectively. Wash thoroughly the hair tresses with warm water to remove shampoo. Remove water along the hair tresses and be ready for the combability test. The wet and dry combability of treated tress was measured by a HM-01 Series hair comb machine (Jiangnan University, China) and combing forces were tested. The treated tresses were firstly tested for wet combability, and wet combing forces were determined. Thereafter, put the tresses into a climate incubator with a constant temperature of 25° C. as well as a constant relative humidity of 60% and keep overnight. Then, Test dry combability and determine dry combing forces according the procedure described above. The reduced combing force of the samples was obtained by using formulation without cationic polymeric conditioner as reference.

The tested samples include: The shampoo formulation comprising cationic corn bran arabinoxylan (cat-AX) prepared in Example 1, the shampoo formulation comprising alkylated cationic corn bran arabinoxylan (C12-cat-AX) prepared in Example 1, and shampoo formulation comprising commercial cationic guar gum ("CGG", guar hydroxypropyltrimonium chloride, using cationic guar gum G114 from Rhodia). The shampoo formulation comprising commercial cationic guar gum is the same with that comprising cat-AX and C12-cat-AX, except that the polymer conditioner is different.

The Effect of Cationic Corn Bran Arabinoxylan and its Hydrophobically Modified Derivatives on the Wet Combability FIG. 9 shows the effect of cationic corn bran arabinoxylan and its hydrophobically modified derivatives of Example 1 on the wet combability of hair. In the figure, CGG represents commercial cationic guar gum.

From FIG. 9, it can be found that cationic corn bran arabinoxylan and its hydrophobically modified derivative can significantly reduce the wet combing force of hair. This indicates that they have excellent conditioning ability. The ability of cationic arabinoxylan to reduce wet combing force is similar to that of cationic guar gum, whereas the ability of hydrophobically modified cationic arabinoxylans to reduce wet combing force is better than that of cationic guar gum. This may be because hydrophobically modified cationic arabinoxylans were easier to deposit onto hair, and can also facilitate other components like silicone oil to deposit onto hair, thereby considerably reduce wet combing force of hair.

The Effect of Cationic Corn Bran Arabinoxylan and its Hydrophobically Modified Derivatives on the Dry Combability FIG. 10 shows the effect of cationic corn bran arabinoxylan and its hydrophobically modified derivatives on the dry combability.

From FIG. 10, it can be found that cationic corn bran arabinoxylan and its hydrophobically modified derivative can well reduce the dry combing force of hair. This indicates that they have good conditioning ability. The ability of cationic arabinoxylan to reduce dry combing force is a little weaker than that of cationic guar gum, whereas the ability of hydrophobically modified cationic arabinoxylan to reduce dry combing force is stronger than that of cationic guar gum. This may be because hydrophobically modified cationic arabinoxylans were easier to deposit onto hair, and can also facilitate other components like silicone oil to deposit onto hair, thereby considerably reduce dry combing force of hair.

As used herein, the phrases "include", "selected from", and the like includes mixtures or combinations of the specified materials. Terms such as "contain(s)" and the like as used herein are open terms meaning 'including at least' unless otherwise specifically noted.

All references, patents, applications, tests, documents, publications, texts, articles, etc. mentioned herein are incorporated herein by reference. Where a numerical limit or range is stated, the endpoints are included. Also, all values and sub ranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein. In this regard, certain embodiments within the invention may not show every benefit of the invention, considered broadly.

The invention claimed is:

1. A method for preparation of a cationic arabinoxylan, comprising the steps of:
    (1) dissolving an arabinoxylan and 0.5-4.0 wt %, of a strong alkali into water wherein the amount of strong alkali is based on the total weight of the strong alkali, arabinoxylan, and water;
    (2) adding a quaternizing agent with the molar ratio of the quaternizing agent and anhydroxylose unit of the arabinoxylan being from 0.2:1 to 5:1, and reacting for 2-8 h; and
    (3) separating the cationic arabinoxylan as reaction product
    wherein the arabinoxylan is selected from water soluble arabinoxylans extracted from the group consisting of corn bran, wheat bran, corn endosperm, wheat endosperm, barley endosperm, rye endosperm, triticale endosperm and oat endosperm.

2. The method of claim 1, wherein the arabinoxylan has a weight average molecular weight of ≥100,000 g/mol.

3. The method of claim 1, wherein the molar ratio of Araf residues to Xylp residues of the arabinoxylan is 0.4~1.2, 0.5~1.0, 0.5~0.95, 0.5~0.93, 0.6~1.0, 0.6~0.95, 0.6~0.93, 0.7~1.0, 0.7~0.95, or 0.7~0.93.

4. The method of claim 1, wherein the degree of substitution of cationic group of the cationic arabinoxylan is 0.03~1.0, 0.03~0.8, 0.04~0.8, 0.04~0.7, 0.04~0.6, 0.06~0.6, 0.08~0.6, or 03~0.6.

5. The method of claim 1 wherein:
    (1) dissolving an arabinoxylan and 2.1:1-2.8 wt % of a strong alkali into water wherein the amount of strong alkali is based on the total weight of the strong alkali, arabinoxylan, and water;
    (2) adding a quaternizing agent with the molar ratio of the quaternizing agent and anhydroxylose unit of the arabinoxylan being from 2:1 to 4:1, and reacting for 4-7 h, at 20-35° C.

6. The method of claim 1, wherein the weight average molecular weight of the cationic arabinoxylan is ≥100,000 g/mol.

7. The method of claim 1, wherein the molar ratio of Araf residues to Xylp residues of the arabinoxylan is 0.5~1.0.

8. The method of claim 1, wherein the degree of substitution of cationic group of the cationic arabinoxylan is 0.04~0.8.

* * * * *

UNITED STATES PATENT AND TRADEMARK OFFICE
CERTIFICATE OF CORRECTION

PATENT NO. : 10,206,863 B2
APPLICATION NO. : 15/310267
DATED : February 19, 2019
INVENTOR(S) : Cheng Yang and Weiyi Cui Page 1 of 1

It is certified that error appears in the above-identified patent and that said Letters Patent is hereby corrected as shown below:

In the Claims

Column 28,
Line 47, "an arabinoxylan and 2.1:1-2.8 wt %" should read -- an arabinoxylan and 2.0 - 2.8 wt % --.

Signed and Sealed this
Twenty-sixth Day of March, 2019

Andrei Iancu
*Director of the United States Patent and Trademark Office*